United States Patent
Kim et al.

(10) Patent No.: US 8,673,856 B2
(45) Date of Patent: Mar. 18, 2014

(54) OMEGA CONOTOXINS

(75) Inventors: Jae II Kim, Gwangju (KR); Hye Whon Rhim, Seoul (KR); Hyun Jeong Kim, Seoul (KR); Hong Won Suh, Yongin-si (KR); Soung Hun Roh, Gwangju (KR); Jung A Yun, Yongin-si (KR); Seung Kyu Lee, Yeosu-si (KR); Young Jae Eu, Daejeon (KR); Heung Sik Na, Seoul (KR)

(73) Assignee: Anygen Co., Ltd., Gwangju (KR)

( * ) Notice: Subject to any disclaimer, the term of this patent is extended or adjusted under 35 U.S.C. 154(b) by 709 days.

(21) Appl. No.: 12/513,182

(22) PCT Filed: Nov. 2, 2007

(86) PCT No.: PCT/KR2007/005519
§ 371 (c)(1),
(2), (4) Date: May 7, 2009

(87) PCT Pub. No.: WO2008/054171
PCT Pub. Date: May 8, 2008

(65) Prior Publication Data
US 2010/0056456 A1    Mar. 4, 2010

(30) Foreign Application Priority Data
Nov. 4, 2006    (KR) .................. 10-2006-0108624

(51) Int. Cl.
*A61K 38/16* (2006.01)
*A61K 38/00* (2006.01)
*C07K 14/00* (2006.01)

(52) U.S. Cl.
USPC ................ 514/17.4; 514/21.3; 530/324

(58) Field of Classification Search
USPC .................. 514/17.4, 21.3; 530/324
See application file for complete search history.

(56) References Cited

FOREIGN PATENT DOCUMENTS

| WO | WO 97/01351 | * | 1/1997 | ............. A61K 38/17 |
|----|-------------|---|--------|------|
| WO | WO 02/07675 |   | 1/2002 | |
| WO | WO 2011/07675 | * | 1/2011 | |

OTHER PUBLICATIONS

Williams et al., 2008, Ziconotide: an update and review, Expert. Opin. Pharmacother., 9(9): 1575-1583.*
Bingham et al., 2010, Drugs from slugs—past, present and future perspectives of _—conotoxin research, Chemico-Biological Interactions, 183: 1-18.*
Adams et al., "ω-Conotoxin CVID Inhibits a Pharmacologically Distinct Voltage-Sensitive Calcium Channel Associated with Transmitter Release from Preganglionic Nerve Terminals," J. Biol. Chem. 278:4057-4062, 2003.
Dai et al., "The Synthesis of SO-3, a Conopeptide with High Analgesic Activity Derived from *Conus striatus*," J. Nat. Prod. 66:1276-1279, 2003.
Lewis et al., "Novel ω-Conotoxins from *Conus catus* Discriminate Among Neuronal Calcium Channel Subtypes," J. Biol. Chem. 275:35335-35344, 2000.
Mould et al., "The $a_2\delta$ Auxiliary Subunit Reduces Affinity of ω-Conotoxins for Recombinant N-Type ($Ca_v2.2$) Calcium Channels," J. Biol. Chem. 279:34705-34714, 2004.
Nadasdi et al., "Structure-Activity Analysis of a Conus Peptide Blocker of N-Type Neuronal Calcium Channels," Biochem. 34:8076-8081, 1995.
International Search Report from International Application No. PCT/KR2007/005519, dated Jan. 11, 2008.

* cited by examiner

*Primary Examiner* — Amber D Steele
(74) *Attorney, Agent, or Firm* — Clark & Elbing LLP

(57) ABSTRACT

The present invention relates to a method for increasing the binding reversibility of a ω-conotoxin to a N-type calcium channel, which comprises preparing a ω-conotoxin having a Ile and/or Ala residue at a position of amino acid (11 and/or 12), respectively in the second loop between cysteine residues (2 and 3) of the ω-conotoxin represented by the formula I, such that the prepared ω-conotoxin has the increased binding reversibility to N-type calcium channel. In addition, the present invention relates to a novel ω-conotoxin and a pharmaceutical composition having plausible properties in view of blocking activity to and specificity to N-type calcium channel, and dramatically improved binding reversibility to N-type calcium channel.

2 Claims, 23 Drawing Sheets

Oxidative folding of linear FVIA

Purification of oxidized FVIA

B  CD spectrums of FVIA analoges

MVIIA

FVIA

A

B

Backbone structure comparison

FVIA

MVIIA

| FVIA | C | KGTGKS | C | SRIAYN | CC | TGS | C | RSGK | C-NH$_3$ |
|---|---|---|---|---|---|---|---|---|---|
| MVIIA | C | KGKGAK | C | SRLMYD | CC | TGS | C | RSGK | C-NH$_3$ |

The position of important residues

MVIIA - Tyr13, Lys2, Arg10, Leu11, Arg21  (Nielsen et al. 2000)

von Frey hair test

Mean arterial pressure

US 8,673,856 B2

OMEGA CONOTOXINS

CROSS-REFERENCE TO RELATED APPLICATIONS

This application claims priority under 35 U.S.C. §371 from international application PCT/KR2007/005519, filed Nov. 2, 2007, which claims priority from Korean Patent Application 10-2006-0108624, filed Nov. 4, 2006.

BACKGROUND OF THE INVENTION

1. Field of the Invention

The present invention relates to novel ω-conotoxin peptides, more particularly, to novel ω-conotoxin peptides and its uses as well as methods for increasing the binding reversibility of a ω-conotoxin to N-type calcium channel.

2. Description of the Related Art

Cone snails represent a diverse family of marine mollusks that use venom for prey capture. The venom of each species contains a unique array of more than 100 peptides, whose pharmaceutical potential remain largely unexploited. Different classes of conotoxins have evolved to target ion channels and receptors for the successful capture of fish, mollusks, or worms [1-6].

One important class, the ω-conotoxins isolated from piscivorous species, inhibits neuronal voltage-sensitive calcium channels (VSCC) found in mammals. ω-Conotoxins have selectivity for N-type or P/Q-type VSCCs, making them widely used research tools for defining the distribution and role of neuronal VSCCs [7]. In addition to their use as research tools, animal studies have shown that ω-Conotoxins that target N-type VSCCs have clinical potential in ischemic brain injury and pain.

However, ω-Conotoxins presently available are not ideal therapeutics, despite their selectivity and potency and the dominant role of N-type VSCCs at synapses in carrying nociceptive information in the spinal cord.

For example, strong N-type VSCC selective blocker, GVIA, dissociates slowly from N-type VSCCs and, accordingly, may be difficult to administer in a clinical setting [8]. Another ω-Conotoxins MVIIA causes a variety of neurological side effects of unknown origin [9-11]. It was reported that MVIIA have more specificity on central N-type isoform than peripheral, although peripheral N-type isoform directly acting on pain signaling. CVID is more selective on the peripheral isoform than the central, therefore had fewer side effects than MVIIA [12-14]. Other ω-conotoxins are less selective for N-type VSCCs and are not considered useful therapeutic candidates.

On residue scanning experiments of N-type VSCCs blocker, $Tyr^{13}$, $Lys^2$, $Arg^{10}$, $Leu^{11}$, $Arg^{21}$, N-term and C-term amide are important on affinity to channels [7, 15]. Recently, it has reported that $Arg^{10}$ has also important role on reversibility of molecules. Substitution of $Arg^{10}$ to $Lys^{10}$ reduces reversibility significantly [14]. Although reversibility is closely correlated with affinity, dissociation of the two properties can be possible [16]. And the improvements on reversibility give potentials of better pain killer drug.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel ω-conotoxins for overcoming problems associated with conventional ω-conotoxins, in particular, low specificity to N-type calcium channel and low reversibility. As a result, we have isolated novel ω-conotoxins from *Conus Flavidus* in Korea, which are completely free from two shortcomings of conventional conotoxins and also exhibit significant activities as blockers to N-type calcium channel. In addition, we have made further studies to reveal structures and functions of the novel ω-conotoxins, thereby elucidating pivotal amino acid residues to reversibility of ω-conotoxins.

Accordingly, it is an object of this invention to provide a method for increasing the binding reversibility of a ω-conotoxin to a N-type calcium channel.

It is another object of this invention to provide an isolated, synthetic or recombinant ω-conotoxin peptide.

It is still another object of this invention to provide a nucleic acid molecule encoding ω-conotoxin peptide.

It is further object of this invention to provide a pharmaceutical composition for preventing or treating diseases, disorders or conditions associated with N-type calcium channel activity.

It is still further object of this invention to provide a method for preventing or treating diseases, disorders or conditions associated with N-type calcium channel activity in a subject.

It is another object of this invention to provided a use of the ω-conotoxin for manufacturing a medicament for preventing or treating diseases, disorders or conditions associated with N-type calcium channel activity.

Other objects and advantages of the present invention will become apparent from the following detailed description together with the appended claims and drawings.

BRIEF DESCRIPTION OF THE DRAWINGS

In FIG. 2B, D analog, LM analog, FM chimera and MF chimera correspond to FVIA[N14D], FVIA[I11L, A12M], chimera-FMFF and chimera-MFMM, respectively in Table 4.

In FIG. 7B, the box represents essential residues of MVIIA in activity.

FIG. 10B demonstrates the dose-dependent effects of FVIA. Bar, standard error of mean. *, P value compared with control (*P<0.05, P<0.01, *P<0.001).

FIG. 11B is % MPE graphs corresponding to the results of FIG. 11A.

DETAILED DESCRIPTION OF THIS INVENTION

Figure 1A:
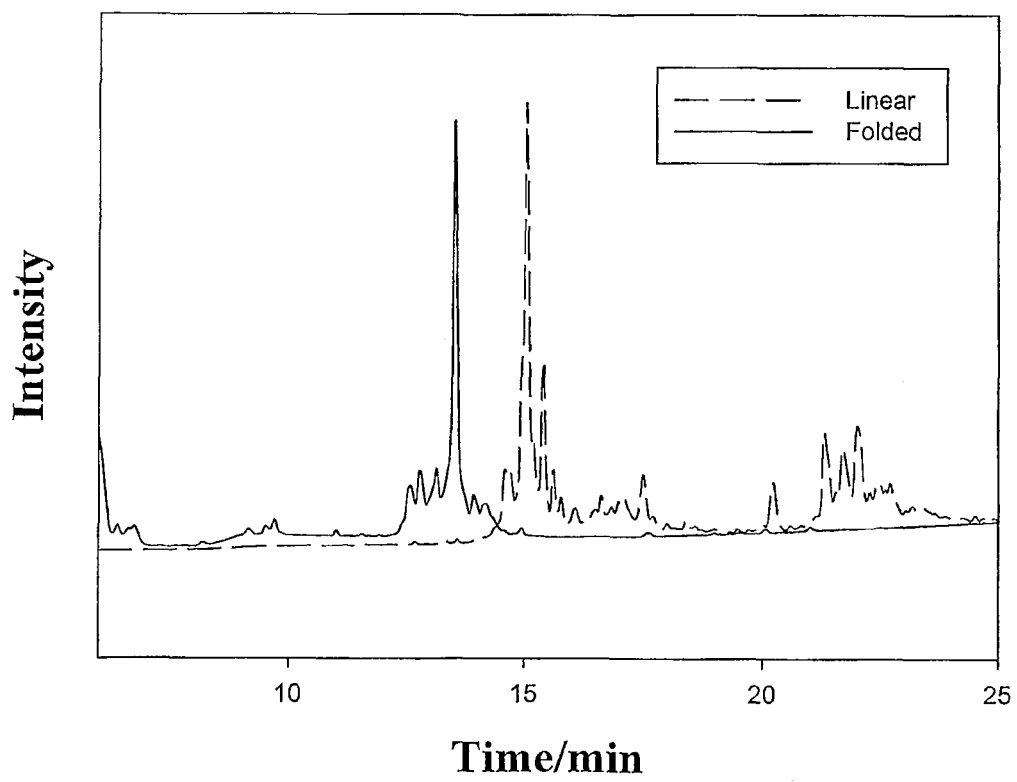
FIGS. 1A and 1B represent reversed-phase HPLC chromatograms of linear, cyclized (FIG. 1A) and purified FVIA (FIG. 1B). Cyclization condition: linear peptide 0.02 mM, GSSG 0.1 mM, GSH 1 mM, 1 mM EDTA, 50 mM $NH_4OAc$, and 1 M $(NH_4)_2SO_4$ (pH 7.8)

In one aspect of this invention, there is provided a method for increasing the binding reversibility of a ω-conotoxin to a N-type calcium channel, which comprises preparing a ω-conotoxin having a Ile and/or Ala residue at a position of amino acid 11 and/or 12, respectively in the second loop between cysteine residues 2 and 3 of the ω-conotoxin represented by the following general formula I, such that the prepared ω-conotoxin has the increased binding reversibility to N-type calcium channel:

Formula I

Cys-Lys-$Xaa_1$-$Xaa_2$-Gly-$Xaa_3$-$Xaa_4$-Cys-$Xaa_5$-$Xaa_6$-$Xaa_7$-$Xaa_8$-Tyr-$Xaa_9$-Cys-Cys-$Xaa_{10}$-$Xaa_{11}$-$Xaa_{12}$-Cys-$Xaa_{13}$-$Xaa_{14}$-$Xaa_{15}$-$Xaa_{16}$-Cys  (SEQ ID NO:6)

wherein $Xaa_1$-$Xaa_{16}$ represent any amino acid residue.

The present inventors have made intensive researches to develop novel ω-conotoxins for overcoming problems associated with conventional ω-conotoxins, in particular, low specificity to N-type calcium channel and low reversibility. As a result, we have isolated novel ω-conotoxins from *Conus Flavidus* in Korea, which are completely free from two shortcomings of conventional conotoxins and also exhibit significant activities as blockers to N-type calcium channel. In addition, we have made further studies to reveal structures and functions of the novel ω-conotoxins, thereby elucidating pivotal amino acid residues to reversibility of ω-conotoxins.

Although the present method is expressed herein by a method for increasing the binding reversibility of a ω-conotoxin to N-type calcium channel, it may be alternatively expressed by a method for preparing a ω-conotoxin with increasing the binding reversibility to N-type calcium channel.

The term used herein "reversibility" or "binding reversibility" is intended to express dissociation rates of ω-conotoxins from N-type calcium channel. The reversibility of ω-conotoxins is generally analyzed by washing-out experiments as described in Examples. There is no intended distinction between the terms "reversibility" and "recovery" and these terms will be used interchangeably herein.

Although there had been already proposed ω-conotoxins that strongly inhibit N-type calcium channels, they usually exhibit worse binding reversibility to N-type calcium channels to be very likely to induce side or adverse effects upon administration to mammals, which severely restricts their application to human.

The present invention is directed to overcome such drawbacks of conventional conotoxins (e.g., GVIA and MVIIA) by providing novel ω-conotoxins with dramatically enhanced reversibility. In addition, the ω-conotoxins of the present invention have excellent blocking potency and specificity to N-type calcium channels.

As such, the theoretical basis of the superiority of the present ω-conotoxins in both reversibility and ion channel inhibition activity is the scientific findings that the binding reversibility and affinity can be separated although two properties are closely correlated [16].

The amino acid residues crucial for reversibility of the present ω-conotoxins are positioned at amino acid 11 and 12 in the general formula I. As clearly demonstrated in Examples, ω-conotoxins exhibit significantly high reversibility to N-type calcium channel only when they have Ile and/or Ala residues at amino acid 11 and 12, respectively. For example, where Ile and Ala are substituted with similar R-group-containing Leu and Met, respectively, ω-conotoxins show greatly reduced reversibility.

A variety of previously published reports had suggested that the positioning of Leu at amino acid 11 of ω-conotoxins is responsible for their stronger ion channel inhibition activities. In contrast, according to the present invention, ω-conotoxins having Ile at amino acid 11 instead of Leu exhibit not only blocking activities similar to conventional ω-conotoxins but also much higher reversibility than conventional ω-conotoxins. In this connection, the present invention takes a giant step to provide new paradigms in ω-conotoxin technology.

In the general formula I, six Cys residues are determinants to ω-conotoxins. In addition, $Lys^2$, $Gly^5$ and $Tyr^{13}$ residues indicated are essential for ion channel inhibition activities of ω-conotoxins.

According to a preferred embodiment, six Cys residues form totally three disulfide bonds. More preferably, the disulfide bonds are formed between the first Cys and fourth Cys residues, between the second Cys and fifth Cys residues, and between the third Cys and sixth Cys residues. Such disulfide bonding patterns are typical in ω-conotoxins and crucial for activities of ω-conotoxins.

The structure of ω-conotoxins is typically described with four loops:

```
C_____C_____CC_____C_____C
   1     2     3     4
```

The four loops are shown underlined.

The present invention is drawn to provide an interesting discovery that Ile and/or Ala residues at positions of amino acid 11 and/or 12, respectively in the second loop between cysteine residues 2 and 3 are implicated in reversibility of ω-conotoxins to N-type calcium channel.

According to a preferred embodiment, both residues positioned at amino acid 11 and 12 are Ile and Ala, respectively.

According to a preferred embodiment, $Xaa_1$ is Gly, Ala or Ser; $Xaa_2$ is Thr, Ala, Lys or Arg; $Xaa_3$ is Lys or Ala; $Xaa_4$ is Ser, Pro, hydroxyproline or Lys; $Xaa_5$ is Ser or Arg; $Xaa_6$ is Arg or Lys; $Xaa_9$ is Asn or Asp; $Xaa_{10}$ is Thr or Ser; $Xaa_{11}$ is Gly, Ala or Ser; $Xaa_{12}$ is Ser, Gly, Ala or Thr; $Xaa_{13}$ is Arg or Gly-Arg; $Xaa_{14}$ is Ser or Arg; $Xaa_{15}$ is Gly, Ala or Ser; and $Xaa_{16}$ is Lys or Arg. More preferably, $Xaa_6$ is Arg, $Xaa_{13}$ is Arg.

According to a more preferred embodiment, $Xaa_1$ is Gly or Ser; $Xaa_2$ is Thr or Lys; $Xaa_3$ is Lys or Ala; $Xaa_4$ is Ser or Lys; $Xaa_5$ is Ser or Arg; $Xaa_6$ is Arg; $Xaa_9$ is Asn or Asp; $Xaa_{10}$ is Thr; $Xaa_{11}$ is Gly; $Xaa_{12}$ is Ser; $Xaa_{13}$ is Arg; $Xaa_{14}$ is Ser; $Xaa_{15}$ is Gly; and $Xaa_{16}$ is Lys or Arg.

According to a more preferred embodiment, $Xaa_2$ is Thr or Lys; $Xaa_3$ is Lys or Ala; $Xaa_4$ is Ser or Lys; $Xaa_5$ is Ser or Arg; $Xaa_6$ is Arg; $Xaa_9$ is Asn or Asp; $Xaa_{10}$ is Thr, $Xaa_{11}$ is Gly; $Xaa_{12}$ is Ser; $Xaa_{13}$ is Arg; $Xaa_{14}$ is Ser; $Xaa_{15}$ is Gly; and $Xaa_{16}$ is Lys or Arg.

In a specific example of the present invention, the ω-conotoxin with the increased binding reversibility to N-type calcium channel comprises the amino acid sequence set forth in SEQ ID NOs: 1, 2 or 3.

Specifically, the ω-conotoxin having the amino acid sequence set forth in SEQ ID NO:2 is prepared by substituting amino acid residues at positions of 11 and 12 of MVIIA with Ile and Ala, respectively, in accordance with the present invention. This analogue shows not only plausible calcium channel inhibition activity but also about 2-fold higher recovery than MVIIA, as demonstrated in Examples.

According to the most preferred embodiment, the ω-conotoxin with the increased binding reversibility to N-type calcium channel comprises the amino acid sequence set forth in SEQ ID NO:1.

According to a preferred embodiment, the ω-conotoxin in the general formula I has an amide-modified C-terminal (Cys residue).

In another aspect of this invention, there is provided an isolated, synthetic or recombinant ω-conotoxin peptide in which the second loop between cysteine residues 2 and 3 of the ω-conotoxin peptide comprises the following general formula II:

Formula II $$Xaa_5\text{-}Xaa_6\text{-}Ile\text{-}Ala\text{-}Tyr\text{-}Xaa_9 \qquad (SEQ\ ID\ NO:7)$$

wherein $Xaa_5$-$Xaa_6$ and $Xaa_9$ represent any amino acid residue.

The ω-conotoxin of the present invention is provided on the basis of our finding that Ile and Ala residues in the second loop are essential for enhanced binding reversibility to N-type calcium channel.

Preferably, each of the first, third and fourth loops of the ω-conotoxin of the present invention corresponds to the loop of a naturally occurring ω-conotoxin peptide.

According to a preferred embodiment, $Xaa_5$ is Ser or Arg; $Xaa_6$ is Arg or Lys; and $Xaa_9$ is Asn or Asp. More preferably, $Xaa_5$ is Ser; $Xaa_6$ is Arg; and $Xaa_9$ is Asn.

According to a preferred embodiment, the ω-conotoxin peptide of the present invention comprises the amino acid sequence represented by the following general formula III:

Formula III $$\begin{aligned}&\text{Cys-Lys-}Xaa_1\text{-}Xaa_2\text{-Gly-}Xaa_3\text{-}Xaa_4\text{-Cys-}Xaa_5\text{-}Xaa_6\text{-}\\&\text{Ile-Ala-Tyr-}Xaa_9\text{-Cys-Cys-}Xaa_{10}\text{-}Xaa_{11}\text{-}Xaa_{12}\text{-}\\&\text{Cys-}Xaa_{13}\text{-}Xaa_{14}\text{-}Xaa_{15}\text{-}Xaa_{16}\text{-Cys}\end{aligned} \qquad (SEQ\ ID\ NO:8)$$

wherein $Xaa_1$ is Gly or Ser; and $Xaa_2$-$Xaa_6$ and $Xaa_9$-$Xaa_{16}$ is any amino acid residue.

According to a preferred embodiment, six Cys residues in the formula III form totally three disulfide bonds. More preferably, the disulfide bonds are formed between the first Cys and fourth Cys residues, between the second Cys and fifth Cys residues, and between the third Cys and sixth Cys residues, Such disulfide bonding patterns are typical in ω-conotoxins and crucial for activities of ω-conotoxins.

According to a preferred embodiment, $Xaa_2$ is Thr, Ala, Lys or Arg; $Xaa_3$ is Lys or Ala; $Xaa_4$ is Ser, Pro, hydroxyproline or Lys; $Xaa_5$ is Ser or Arg; $Xaa_6$ is Arg or Lys; $Xaa_9$ is Asn or Asp; $Xaa_{10}$ is Thr or Ser; $Xaa_{11}$ is Gly, Ala or Ser; $Xaa_{12}$ is Ser, Gly, Ala or Thr; $Xaa_{13}$ is Arg or Gly-Arg; $Xaa_{14}$ is Ser or Arg; $Xaa_{15}$ is Gly, Ala or Ser; and $Xaa_{16}$ is Lys or Arg.

More preferably, $Xaa_6$ is Arg; and $Xaa_{13}$ is Arg.

According to a more preferred embodiment, $Xaa_2$ is Thr or Lys; $Xaa_3$ is Lys or Ala; $Xaa_4$ is Ser or Lys; $Xaa_5$ is Ser or Arg; $Xaa_6$ is Arg; $Xaa_9$ is Asn or Asp; $Xaa_{10}$ is Thr; $Xaa_{11}$ is Gly; $Xaa_{12}$ is Ser; $Xaa_{13}$ is Arg; $Xaa_{14}$ is Ser; $Xaa_{15}$ is Gly; and $Xaa_{16}$ is Lys or Arg.

According to a more preferred embodiment, $Xaa_2$ is Thr or Lys; $Xaa_3$ is Lys or Ala; $Xaa_4$ is Ser or Lys; $Xaa_5$ is Ser or Arg; $Xaa_6$ is Arg; $Xaa_9$ is Asn or Asp; $Xaa_{10}$ is Thr; $Xaa_{11}$ is Gly; $Xaa_{12}$ is Ser; $Xaa_{13}$ is Arg; $Xaa_{14}$ is Ser; $Xaa_{15}$ is Gly; and $Xaa_{16}$ is Lys or Arg.

According to still more preferred embodiment, the ω-conotoxin comprises the amino acid sequence set forth in SEQ ID NOs:1, 2 or 3.

More preferably, the ω-conotoxin of the present invention comprises the amino acid sequence set forth in SEQ ID NO:1.

The ω-conotoxin of the present invention includes peptides in which one or more of amino acids have side chain modification. Examples of side chain modifications include modifications of amino groups such as by reductive alkylation; amidination with methylacetimidate; acylation with acetic anhydride; carbamolyation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl group of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residue may be modified by, for example, hydroxylation in the 4-position.

The ω-conotoxin of the present invention is specifically bound to N-type calcium channel to block the ion channel. The ion channel blockers are classified to pore blockers and gate modifiers. The ω-conotoxin of the present invention belongs to pore blockers.

The ω-conotoxin of the present invention may be prepared in accordance with a variety of methods. For example, it may be produced by gene cloning methods or solid-phase synthesis techniques.

More specifically, the nucleotide sequences coding for ω-conotoxins are transformed into suitable host cells and expressed to produce ω-conotoxin peptides (see Sambrook, J. et al., *Molecular Cloning. A Laboratory Manual*, 3rd ed. Cold Spring Harbor Press (2001)).

Alternatively, the ω-conotoxin of the present invention may be produced in accordance with solid-phase synthesis techniques known to one of skill in the art (Merrifield, *J. Amer. Chem. Soc.* 85:2149-54 (1963); Stewart, et al., *Solid Phase Peptide Synthesis*, 2nd. ed., Pierce Chem. Co.: Rockford, 111 (1984)).

According to a preferred embodiment, the ω-conotoxin in the general formula I has an amide-modified C-terminal (Cys residue).

The ω-conotoxin of the present invention exhibits plausible properties in view of blocking activity to and specificity to N-type calcium channel, and dramatically improved binding reversibility to N-type calcium channel.

The ω-conotoxin of the present invention has excellent therapeutic efficacies on inflammatory and neuropathic pains. Unlikely, the present ω-conotoxin is much less implicated in analgesic effects on nociceptive pains.

Since nociceptive pains are one of defense mechanisms against outside harmful stimuli, it is not desirable to excessively inhibit nociceptive pains. It is generally known to one of skill in the art that excellent analgesic drug candidates exhibit pain relief potency selectively on inflammatory and neuropathic pains, one of pathologic pains.

In these regards, the ω-conotoxin of the present invention can be highlighted as a promising analgesic drug candidate.

In addition to this, the ω-conotoxin of the present invention has little or no side effects in the senses that it has greatly improved binding reversibility to N-type calcium channel and much less influence on the cardiovascular system, as illustrated in Examples.

In still another aspect of this invention, there is provided a nucleic acid molecule comprising the nucleotide sequence encoding the amino acid sequence of SEQ ID NO:1.

The term "nucleic acid molecule" used herein refers to a deoxyribonucleotide or ribonucleotide polymer (including gDNA, cDNA and mRNA) in either single or double-stranded form, including known analogs of natural nucleotides unless otherwise indicated (Scheit, *Nucleotide Analogs*, John Wiley, New York (1980); Uhlman and Peyman, Chemical Reviews, 90:543-584 (1990)).

According to a preferred embodiment, the nucleic acid molecule encoding the ω-conotoxin of the present invention comprises the nucleotide sequence set forth in SEQ ID NO:4.

In a further aspect of this invention, there is provided a vector carrying a nucleic acid molecule comprising the nucleotide sequence encoding the amino acid sequence of SEQ ID NO:1.

The vector system of this invention may be constructed according to the known methods in the art as described in Sambrook et al., *Molecular Cloning, A Laboratory Manual*, Cold Spring Harbor Laboratory Press (2001), which is incorporated herein by reference.

Typically, the vector may be constructed for cloning or expression. In addition, the vector may be constructed for use in prokaryotic or eukaryotic host cells.

For example, where the vector is constructed for expression in prokaryotic cells, it generally carries a strong promoter to initiate transcription (e.g., $p_L^\lambda$ promoter, $P_R^\lambda$ promoter, rac5 promoter, lacUV5 promoter, lpp promoter, trp promoter, amp promoter, recA promoter, SP6 promoter, lac promoter, tac promoter and T7 promoter), a ribosome binding site or translation initiation and a transcription/translation termination sequence. In particular, where *E. coli* is used as a host cell, a promoter and operator in operon for tryptophan biosynthesis in *E. coli* (Yanofsky, C., *J. Bacteriol.*, 158:1018-1024 (1984)) and a leftward promoter of phage λ ($p_L^\lambda$ promoter, Herskowitz, I. and Hagen, D., *Ann. Rev. Genet.*, 14:399-445 (1980)) may be employed as a control sequence.

Numerous conventional vectors used for prokaryotic cells are known to those of skill in the art, and the selection of an appropriate vector is a matter of choice. Conventional vector used in this invention includes pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, λgt4λB, λ-charon, λΔz1 and M13, but not limited to.

For example, where the expression vector is constructed for eukaryotic host cell, inter alia, animal cell, a promoter derived the genome of mammalian cells (e.g., metallothionein promoter) or mammalian virus (e.g., adenovirus late promoter; vaccinia virus 7.5K promoter, SV40 promoter, cytomegalovirus promoter and tk promoter of HSV) may be used. The vector generally contains a polyadenylation site of the transcript. The example of commercial virus-based vectors includes pcDNA 3 (Invitrogen; containing cytomegalo virus promoter and polyadenylation signal), pSI (Promega; containing SV 40 promoter and polyadenylation signal), pCI (Promega; containing cytomegalo virus promoter and polyadenylation signal), and pREP7 (Invitrogen; RSV promoter and SV 40 polyadenylation signal).

In addition, the expression vector of this invention further comprises a nucleotide sequence to conveniently purify the fusion protein expressed, which includes but not limited to, glutathione S-transferase (Pharmacia, USA), maltose binding protein (NEB, USA), FLAG (IBI, USA) and 6×His (hexahistidine; Quiagen, USA).

According to a preferred embodiment of this invention, the fusion protein is purified by affinity chromatography. For example, in case of using glutathione S-transferase, elution buffer containing glutathione is employed and in case of using 6×His, Ni-NTA His-binding resin (Novagen, USA) is generally employed to purify the fusion protein of interest in a rapid and feasible manner.

It is preferable that the expression vector of this invention carries one or more markers which make it possible to select the transformed host, for example, genes conferring the resistance to antibiotics such as ampicillin, gentamycine, chloramphenicol, streptomycin, kanamycin, neomycin, geneticin and tetracycline, URA3 gene, genes conferring the resistance to any other toxic compound such as certain metal ions.

In still further aspect of this invention, there is provided a transformant harboring the vector.

The hosts useful in preparing the transformant are well known to those skilled in the art. For example, as prokaryotic host, *E. coli* JM109, *E. coli* BL21, *E. coli* RR1, *E. coli* LE392, *E. coli* B, *E. coli* X 1776, *E. coli* W3110, *Bacillus subtilis*, *Bacillus thurigensis*, *Salmonella typhimurium*, *Serratia marcescens* and various *Pseudomonas*, *Corynebacterium* and *Streptomyces* may be employed. As eukaryotic cell, yeast (*Saccharomyce cerevisiae*), insect cell, human cell (e.g., CHO, W138, BHK, COS-7, 293, HepG2, 3T3, RIN and MDCK cell lines) and plant cell may be used.

The transformation of a host cell can be carried out by a large number of methods known to one skilled in the art. For example, in case of using prokaryotic cells as host, $CaCl_2$ method (Cohen, S. N. et al., *Proc. Natl. Acac. Sci. USA*, 9:2110-2114 (1973)), Hanahan method (Cohen, S. N. et al., *Proc. Natl. Acac. Sci. USA*, 9:2110-2114 (1973); and Hanahan, D., *J. Mol. Biol.*, 166:557-580 (1983)) and electrophoresis (Dower, W. J. et al., *Nucleic. Acids Res.*, 16:6127-6145 (1988)) can be used for transformation. Also, in case of using eukaryotic cells as host, microinjection (Capecchi, M. R., *Cell*, 22:479 (1980)), calcium phosphate precipitation (Graham, F. L. et al., *Virology*, 52:456 (1973)), electrophoresis (Neumann, E. et al., *EMBO J.*, 1:841 (1982)), liposome-mediated transfection (Wong, T. K. et al., *Gene*, 10:87 (1980)), DEAE-dextran treatment (Gopal, *Mol. Cell Biol.*, 5:1188-1190 (1985)), and particle bombardment (Yang et al., *Proc. Natl. Acad. Sci.*, 87:9568-9572 (1990)) can be use for transformation.

Expression vectors in host cells express the ω-conotoxin of interest. For example, if expression vector carries lac promoter, the induction of expression can be performed using IPTG (isopropyl-β-D-thiogalactopyranoside).

In another aspect of this invention, there is provided a pharmaceutical composition for preventing or treating diseases, disorders or conditions associated with N-type calcium channel activity, comprising (a) a therapeutically effective amount of the ω-conotoxin of the present invention; and (b) a pharmaceutically acceptable carrier.

In still another aspect of this invention, there is provided a method for preventing or treating diseases, disorders or conditions associated with N-type calcium channel activity in a subject, which comprises administering to the subject in need of such treatment a pharmaceutical composition comprising (a) a therapeutically effective amount of the ω-conotoxin of the present invention; and (b) a pharmaceutically acceptable carrier.

In a further aspect of this invention, there is provided a use of the ω-conotoxin of the present invention for manufacturing a medicament for preventing or treating diseases, disorders or conditions associated with N-type calcium channel activity.

Since the present pharmaceutical composition comprises the ω-conotoxin of the present invention described above, the common descriptions between them are omitted in order to avoid undue redundancy leading to the complexity of this specification.

The pharmaceutical composition of this invention can be used to prevent or treat various diseases, disorders or conditions associated with N-type calcium channel activity. The diseases, disorders or conditions associated with N-type calcium channel activity are caused by the disorder or undesirable activity of N-type calcium channel.

According to a preferred embodiment, the disease, disorder or condition prevented or treated by the present pharmaceutical composition is chronic pain conditions such as neuropathic pain, diabetic peripheral neuropathy, post-herpetic neuralgia, trigeminal neuralgia, AIDS related neuropathy, cancer pain, inflammatory pain, osteoarthritis pain, rheumatoid arthritis pain and fibromyalgia; acute pain; post-operative pain; mood disorders; anxiety disorders such as generalized anxiety disorders, social anxiety disorder, panic disorder, obsessive compulsive disorder and post-traumatic stress syndrome; depression; addiction disorders such as cocaine dependence and withdrawal, opioid dependence and withdrawal, alcohol dependence and withdrawal and nicotine dependence and withdrawal; gastrointestinal disorders such as inflammatory bowel disease and irritable bowel syndrome; and genitourinary disorders such as urinary incontinence, interstitial colitis and sexual dysfunction; neurotoxic injury associated with hypoxia, anoxia or ischemia such as neurotoxic injury associated with stroke, cerebrovascular accident, brain or spinal cord trauma, myocardial infarct, physical trauma, drownings, suffocation, perinatal asphyxia or hypoglycemic events.

Most preferably, the pharmaceutical composition of this invention is to use for relieving various pains. In particular, the pharmaceutical composition is administered to inflammatory or neuropathic pains rather than nociceptive pains.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative.

The pharmaceutical composition according to the present invention may be orally or parentally administered. For non-oral administration, intravenous injection, subcutaneous injection, intrathecal injection, intraperitoneal injection, intracerebral injection and intramuscular injection may be employed.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. Generally, suitable dosage unit for human host is to administer with the pharmaceutical composition in 0.0001-100 mg/kg (body weight). The term used herein "therapeutically effective amount" in conjunction with ω-conotoxins means a sufficient dose to prevent or treat diseases, disorders or conditions associated with N-type calcium channel activity described hereinabove.

According to the conventional techniques known to those skilled in the art, the pharmaceutical composition comprising the recombinant adenovirus according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The pharmaceutical composition of this invention exerts plausible blocking activity to and specificity to N-type calcium channel, and dramatically improved binding reversibility to N-type calcium channel. Furthermore, the pharmaceutical composition has excellent therapeutic efficacies on a multitude of disorders and conditions associated with disordered N-type calcium channel activity, preferably, pains. In addition to this, the pharmaceutical composition of the present invention has little or no side effects in the senses that it has greatly improved binding reversibility to N-type calcium channel and much less influence on the cardiovascular system, as illustrated in Examples.

In these regards, the pharmaceutical composition of this invention can be highlighted as a promising drug candidate, inter alia, analgesic drug candidate.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Toxin Extraction and Sequencing

*Conus Flavidus* was collected from the coast of the Je-Ju Island of Korea. Venom duct, radula sac and bulb contents were extracted with 30% acetic acid/water and centrifuged. Supernatants was lyophilized and stored at −20° C. prior to use. A portion of the crude venom extract was fractionated on a semi-preparative RP-HPLC column (25×250 mm C18, shimpack) eluted at 14 ml/min with a linear gradient of 1% solvent B over 65 min (solvent A 100% $H_2O$, solvent B 100% acetonitrile containing 0.1% trifluoracetic acid). Crude venom extract was divided into 8 fractions, and third and fifth fractions were further purified by RP-HPLC. The molecular masses of the peptides were determined by using MALDI-MS (Shimadzu). The samples were prepared with α-cyano-4-hydroxycinnamic acid as matrix. External calibration was performed with angiotensin.

The purified peptide was reduced in the presence of 40 mM DTT and 50 mM ammonium bicarbonate pH7.5 (50° C. for 30 min) before alkylating in the added presence of 1 M 4-vinylpyridine (RT for 1 hour). The alkylated peptide was repurified by RP-HPLC prior to sequence analysis by Edman chemistry on a Procise 491 Protein sequencing system (Applied Biosystems).

Isolation of Genomic DNA

Frozen tissue (0.1 g) of chelyconus fulmen was added to 1 ml cell lysis buffer and Guanidium thiocyanate/EDTA/Sarkosyl (GES) reagent and grinded with glass homogenizer. The mixture was centrifuged at 13,000 rpm for 15 min at room temperature and the supernatant was extracted once with phenol and once with chloroform. The extract obtained thus was centrifuged at 13,000 rpm for 15 min at 4° C. The colorless upper aqueous phase was transferred to a fresh tube, precipitated DNA with same volume isopropanol, and centrifuged for 10 min at 13,000 rpm in a microcentrifuge. The pellet was washed with 70% ethanol and dried. Then, the pellet was resuspended by adding 50 microliter of 10 mM Tris-HCl (pH 8.5).

PCR of Genomic DNA

Conopeptide genes were amplified by Taq DNA polymerase using genomic DNA as templates and primers. Among primer, the 5' primer was designed on the basis of the 3'-end of the intron preceding the toxin region of ω-conotoxin prepropeptide: 5'-CTCTCTCTCTCTCTGCTGGAC-3' (SEQ ID NO: 14). The 3' primer was designed on the basis of the 3' UTR sequence of the ω-conotoxin prepropeptide: 5'-CAGAAAAGGATAGAGCACAGAAGG-3' (SEQ ID NO: 15). PCR condition was 35 cycles of 94° C. for 30 sec, 55° C. for 30 sec and 70° C. for 45 sec.

The DNA fragments amplified were purified using the High Pure PCR product purification kit (Roche Diagnostics). The purified PCR products were cloned into pGEM T-easy vector (Promega) and introduced into *E. coli* (JM109) by electroporation. The transformed cells were plated onto LB plates containing ampicillin and cultured for 24 hr at 37° C. to select colonies. The plasmids were isolated from the cultured colonies and digested with EcoRI to prepare 300-400 bp DNA fragments for sequencing.

Sequencing

The nucleotide sequences of conotoxin cDNAs cloned above were analyzed using ABI PRISM 377 Automated DNA Sequencer (PERKIN ELMER). After sequencing, the nucleotide sequences lacking vector and primer sequences were translated into the amino acid sequences. We determined the nucleotide sequences encoding ω-conotoxin-specific ω-cysteine arrangements as conotoxin genes of chelyconus fulmen.

Peptide Synthesis

Peptide synthesis was conducted on an Applied Biosystems model 433A peptide synthesizer. The linear precursors of FVIA were synthesized by solid phase Fmoc chemistry starting from Fmoc-$NH_2$-Alko resin and using a variety of blocking groups for amino acid protection. After cleavage by trifluoroacetic acid, crude linear peptides were extracted with 2 M acetic acid, diluted to final peptide concentrations of 20 µM in a solution of 0.33 M ammonium acetate, 0.5 M Guanidine-HCl and 2 mM reduced/0.2 mM oxidized glutathione adjusted to pH 8.0 with aqueous $NH_4OH$, and stirred slowly at 4° C. for 5 days. The folding reactions were monitored by HPLC. The crude oxidized products were purified by successive chromatography with CM-cellulose CM-52 and preparative HPLC with $Cl_8$ silica columns. The purity of FVIA was confirmed by analytical HPLC and MALDI-TOF-MS measurements.

CD Measurement

CD spectra were measured on a JASCO J-710 spectropolarimeter in solution (0.01 M sodium phosphate in $H_2O$, pH 7.0) at 20° C. at the concentrations of 0.05 mM for 190-250 nm with a quartz cell of path length 1 mm. The spectra were obtained as an average of 4 scans at a scan speed of 20 nm/min. The spectra are expressed as molecular ellipticity [θ] in deg·cm$^2$·dmol$^{-1}$ [18, 19]

Electrophysiological Recording of Calcium Channel Current

Electrophysiological recordings were achieved using whole-cell patch-clamp techniques at room temperature. Borosilicate glass electrodes with a resistance of 3-4 MΩ were pulled and coated with Sylgard. For the recordings of N-type Ca²⁺ currents, the standard whole-cell patch-clamp method was utilized. For the recording of N-type $Ca^{2+}$ currents, the composition of the internal solution contained (in mM): 130 KCl, 11 EGTA, 10 Hepes, and 5 Mg-ATP (pH 7.4), and the external solution contained: 140 NaCl, 2 $CaCl_2$, 10 glucose, and 10 Hepes (pH 7.4). The current recordings were obtained using an EPC-9 amplifier and Pulse/Pulsefit software program (HEKA, Germany) [20].

Recovery Measurements

Currents were evoked by 200-ms voltage steps to 0 mV from a holding potential of −80 mV. The peptide toxins diluted were perfused at a rate of 2 ml/min. The current measurement during washing out was carried out and continued up to the time of current stability for 5 min. The peptide toxins were added just prior to the first trace (control). Currents were recorded in the same cell during toxin washout. Current records were obtained at 15-sec intervals.

NMR Measurements

NMR spectra were recorded on a Bruker AVANCE 600 spectrometer. Samples for NMR experiments were 7 mM FVIA dissolved in either 90% $H_2O$/10% $^2H_2O$ or 99.96% $^2H_2O$ at pH 3.5 (uncorrected for the isotope effect). All two-dimensional NMR experiments {i.e. DQF-COSY, E-COSY, HOHAHA and NOESY} were carried out using standard pulse sequences and phase cycling at temperature of 288 K and 298 K [21, 22]. HOHAHA spectra were recorded with mixing times of 80 ms and 100 ms. NOESY spectra [23, 24] were recorded with mixing times of 100 ms, 150 ms and 250 ms. Suppression of the solvent resonance in both the NOESY and TOCSY measurements was achieved using the WATERGATE scheme [25]. DQF-COSY [26] and PE-COSY [27] spectra were recorded to obtain the constraints for the torsion angles and stereospecific assignments, respectively. In this case, solvent resonance was suppressed by selective irradiation during the relaxation delay period. The data sizes used for acquisition were 512 (t1)×8192 (t2) for DQF-COSY and PE-COSY and 512×2048 otherwise. Slowly exchanging backbone amide protons were identified by analysis of TOCSY spectra recorded in 99.96% $^2H_2O$ on time scales of 2 hr 30 min, 5 hr, 7 hr 30 min, 10 hr and 24 hr. Chemical shifts were referenced to the methyl resonance of TSP used as an internal standard. Complete sets of two-dimensional spectra were recorded at 288K and 298K (pH 3.5).

Spectra were processed and analyzed with Bruker XWIN-NMR software. Phase-shifted sine-squared window functions were applied before Fourier transformation. Except for PE-COSY, final matrix sizes were 2048×2048 real points. High-resolution DQF-COSY and PE-COSY spectra were strip transformed to 1024×8192.

Experimental Restraints and Structure Calculations

Quantitative determination of the cross-peak intensities was based on the contouring levels. Observed NOE data were classified into four distance ranges, 1.8 to 2.7, 1.8 to 3.5, 1.8 to 5.0 and 1.8 to 6.0 Å, corresponding to strong, medium, weak and very weak NOE values, respectively. Pseudo-atoms were used for the methyl protons or the non-stereospecifically assigned methylene protons. Correcting factors for the use of pseudo-atoms were added to the distance constraints [28]. In addition, 0.5 Å was added to the distance constraints involving methyl protons [29]. For each disulfide bond, three distance constraints, S(i)-S(j), S(i)-$C^β$(j) and S(j)-$C^β$(i), were used with target values set to 2.02(±0.02), 2.99(±0.5) and 2.99(±0.5) Å, respectively [30].

The backbone NH—CoH coupling constants were estimated from the DQF-COSY spectrum and were converted to backbone torsion angle ϕ constraints according to the following rules: for $^3J_{NH-CoH}$ less than 5.5 Hz, the ϕ angle was constrained in the range of −65±25°; for $^3J_{NH-CoH}$ greater than 8.0 Hz, it was constrained in the range of −120±40° [31, 32]. Backbone dihedral constraints were not applied to $^3J_{NH-CoH}$ values between 5.5 and 8.0 Hz. The range of the $χ^1$ side chain torsion angle constraints and the stereospecific assignment of the prochiral β-methylene protons were obtained by using the $^3J_{αβ}$ coupling constants combined with the intraresidue NH—CβH NOEs [33]. The $^3J_{αβ}$ coupling constants were determined from the PE-COSY spectrum in $^2H_2O$. For the $t^2g^3$, $g^2g^3$ and $g^2t^3$ conformations around the $C^α$—$C^β$ bonds, the $χ^1$ side chain torsion angle was constrained in the ranges of −60±30°, 60±30° and 180±30° [34]. The hydrogen bond acceptors for the slowly exchanged amide protons were identified by analyzing the preliminary calculated structures [35, 36]. The distance restraints of hydrogen bonds were added as target values of 1.8-2.3 Å for NH (i)-O (j) and 2.8-3.3 Å for N (i)-O (j), respectively.

All calculations were carried out using the X-PLOR 3.1 program running on a SGI O2 workstation using the X-PLOR 3.851 program [37]. The three-dimensional structures were calculated on the basis of distance and torsion angle constraints experimentally derived with dynamic simulated annealing protocols starting from a template structure with randomized backbone ϕ and ψ tortional angles.

Evaluation of the Structure

The final 20 structure s with the lowest energy and smallest Lennard-Jones van der Wassis energy were chosen. The convergence of the calculated structures was evaluated in terms of the structural parameters. There were RMS deviations from the experimental distance and dihedral constraints, from the energetic statistics ($F_{NOE}$, $F_{tor}$, $F_{repel}$, and $E_{L-J}$), and from the idealized geometry. The structures were analyzed using the PROCHECK_NMR [38], PROMOTIF_NMR [39] and MOLMOL programs [40]. The distributions of the backbone dihedral angles in the final converged structure were evaluated by representation of the Ramachandran dihedral pattern, which indicated the deviations from the allowed (ϕ, ψ) angle limits. The degrees of angular variation among the converged structures were further assessed by using an angular order parameter [5, 41]. The solvent accessible surface areas for the side chains of amino acid residues were calculated with a solvent radius of 1.4 Å.

Construction of FVIA Site Specific Substituted Analogues, Calcium Channel Inhibition and Recovery Analysis Site-specific analogues of FVIA having amino acid sequences of Table 5 were synthesized as method described above. The calcium channel blocking potency and recovery of the FVIA analogues were analyzed according to methods described hereinabove.

Animal Tests for Analgesic Effect

1. Experimental Animals

ICR mice (IcrTacSam: ICR, MJ Co., Seoul, Korea) weighed 23-25 g were used. The mice divided to five mice per cage were adapted for 24 hr under controlled temperature (22±2° C.) and humidity (30 to 50%) and given water and solid feed ad libitum. All experimental mice were allowed to habituate to surrounding environments for 2 hr before pain experiments. Experiments using mice were conducted during day (AM 10:00-PM 17:00) for reducing errors.

2. Intrathecal Injection of FVIA

The intrathecal injection of toxin peptides were performed using 25 μl Hamilton syringe with 30 gage needle according to previously reported methods [50, 51]. The dose of toxin peptides was determined by the observation of spine staining with 1% methylene blue. For our experiments, 5 μl of the FVIA peptide in a concentration of 0.01 μg/5 μl was intrathecally injected.

3. Tail-Flick Test Mice were treated with 5 μl of the FVIA peptide (0.01 μg/5 μl) intrathecally 5 min before testing. The control group was treated only with a physiological saline. Tail-flick test was performed using a model TF6 tail flick device (EMDIE Instrument Co., Maidens Va.). The body of mice was fixed with a hand and their tail was arranged evenly, followed by irradiating lower part of tails with light of an intensity of 3.8 mWatt/cm$^2$ for imposing heat stimuli. The time it takes for mice to flick their tail was recorded.

4. Plantar Test

Mice were treated with 5 μl of the FVIA peptide (0.01 μg/5 μl) intrathecally 5 min before testing. Plantar test was performed using thermal plantar device (Plantar test 7371, Ugo Basile, Italy) to measure the thermal pain threshold. Mice were placed into chambers and adapted to surrounding environment before experiment. They were subjected to heat stimulus by irradiating the plantar of paws with light of an intensity of 90 mWatt/cm$^2$. The latencies of paw withdrawal were measured.

5. Writhing Test (Visceral Pain Model)

Mice were treated with 5 μl of the FVIA peptide (0.01 μg/5 μl) intrathecally 5 min before testing and then intraperitoneally injected with 250 μl of 1.0% acetic acid in saline (0.9% NaCl) and then writhing responses were counted for 30 min.

6. Glutamate-Induced Nociceptive Test

Mice were treated with 5 μl of the FVIA peptide (0.01 μg/5 μl) intrathecally 5 min before testing. Afterwards, mice were habituated in chambers for at least 30 min before glutamate injection (20 μg/5 μl). Following the intrathecal injection of glutamate (Sigma Chemical Co., St. Louis, Mo., USA), mice in a transparent observation chamber (acrylic-plastic, 20 cm in height, 20 cm in diameter) were observed for nociceptive behavior (licking, biting or scratching).

7. Substance P-Induced Nociceptive Test

Mice were treated with 5 μl of the FVIA peptide (0.01 μg/5 μl) intrathecally 5 min before testing. Afterwards, mice were habituated in chambers for at least 30 min before substance P injection (0.7 μg/5 μl). Following the intrathecal injection of substance P (Tocris Cookson Ltd., Bristol, UK), mice in a transparent observation chamber (acrylic-plastic, 20 cm in height, 20 cm in diameter) were observed for nociceptive behavior (licking, biting or scratching).

7. Formalin Test

Formalin test was carried out in accordance with the previously reported method of Hunskaar [52]. Briefly, mice were treated with 5 μl of the FVIA peptide (0.01 μg/5 μl) intrathecally 5 min before testing. Afterwards, 10 μl of 5% formalin in saline (0.9% NaCl) was injected subcutaneously into the plantar surface of the left hindpaw of mice. The counts of behavior activities (licking, biting, scratching or shaking) of mice in a transparent observation chamber (acrylic-plastic, 20 cm in height, 20 cm in diameter) were recorded immediately after injection for the first phase (0-5 min) and the second phase (20-40 min) for a total duration of 40 min.

Analgesic Effect in Neuropathic Pain I. Injury Model of Nerve at the Left Leg

1. Experimental Animals and Neuropathic Pain-Induced Model

All of the experiments followed the ethical guidelines for the International Association for the Study of Pain and the ethical guidelines for animal experiments of Seoul University, School of Dentistry (Korea). Sprague-Dawley male rats weighed 150-200 g (Orient Bio Co., Seoul, Korea) were housed in colony cages and were given a standard laboratory chow and water ad libitum. A 12 h/12 h light-dark cycle was used, with all the treatment being performed during the light period of the cycle (AM 10:00-PM 17:00). The examination of pain behaviors was performed under controlled temperature (20-24° C.) and humidity (40-60%).

Neuropathic pain models were produced in accordance with Kim and Chung method [53]. Briefly, rats were anesthetized using 2-3 vol % enflurane and the regions from the dorsolumber to gluteal regions were shaved. The shaved region was incised along the median line, and then the left paraspinal muscle was ablated from the processus at L4-S2 levels. After the removal of processus pterygoideus so as to be able to see L4-L6 spinal nerves, L5 and L6 spinal nerves were exposed and two positions each were ligated firmly using silk suture No. 5-0. After perfusion with a physiological saline, muscle and skin were sutured. On day 1, 4, 7 and 14 after operation, pain response tests were performed to select rats showing 50% avoidance threshold not more than 2.0 g for intrathecal catheterization.

2. Intrathecal Catheterization

Intrathecal catheterization was carried out as the method reported by Yaksh et al [54]. Briefly, rats were anesthetized by enflurane and their heads were fixed in stereotaxic frames at both external auditory meatuses, followed by performing the dura mater incision. Then, catheter (PE-10) was inserted to the lumbar enlargement and additional 5-cm length was secured to serve a path of drug injection. Animals were allowed for recovery from surgery before testing started. Only rats with no neurological deficits after 5 days of intrathecal catheterization and with motor paralysis at the hind leg by 10-μl injection of 1% lidocaine were used for the experiments. Beginning 1 day of lidocaine injection, rats were administered with conotoxins.

3. Pain Analysis to Mechanical Stimulus

Avoidance response to mechanical stimulus was measured by housing rats in a transparent observation chamber (acrylic-plastic, 8×8×8 cm) with a stainless mesh bottom and habituating rats for about 30 min. Then, rats were subjected to stimulating with von Fray filament (bending force: 0.41, 0.70, 1.20, 2.00, 3.63, 5.50, 8.50 and 15.14 g) the central parts of the soles of legs of each rat according to the up & down method [55, 57]. Only rats showing 50% avoidance threshold not more than 15.14 g in three independent pain response tests before nerve ligation were used for this experiment.

Analgesic Effect in Neuropathic Pain II. Injury Model of Tail Nerve

1. Experimental Animals and Neuropathic Pain-Inducing Operation

Sprague-Dawley male rats weighed 150-200 g were housed in colony cages and were given a standard laboratory chow and water ad libitum. A 12 hr/12 hr light-dark cycle was used, with all the treatment being performed during the light period of the cycle. The examination of pain behaviors was performed under controlled temperature (22-25° C.) and 12 hr/12 hr light-dark cycle.

1.1. Induction of Peripheral Neuropathy

Rats were anesthetized using a mixed gas of 4% enflurane and 950% oxygen. For inducing neuropathic pain at tails, the superior and inferior caudal trunks present in rat tails were exposed, freed carefully from the surrounding tissues and transected at the level between the S1 and S2 spinal nerves. To prevent the possible rejoining of the proximal and distal ends of the severed trunk, about 2-mm piece of the trunk was removed from the proximal end. This surgery eliminated the S1 spinal nerve innervation of the tail via the superior and inferior caudal trunks [56].

1.2. Examination of Neuropathic Pain Behaviors

The behavioral tests were performed according to blind study with researchers having no knowledge of drug administration.

1.2.1. Behavioral Tests for Mechanical Allodynia

Mechanical allodynia was assessed by determining the stiffness (gram) of von Frey hair to induce 50% avoidance response after poking the tail with von Frey hairs (bending force: 0.4, 0.6, 1.0, 2.0, 4.0, 6.0, 8.0 and 15.0 g) as the Up-Down method [55, 57]. The statistically significant decrease in avoidance response threshold compared with those before nerve injury operation was determined as the occurrence of mechanical allodynia.

1.2.2. Behavioral Tests for Cold Allodynia

The tests for cold allodynia were performed by immersing the tail into cold water (4° C.) and recording a tail withdrawal time. Following the tail immersion, the latency of tail withdrawal was measured within a cut-off time of 15 sec. The tests for cold allodynia were repeated five times with 5-min intervals. The faster withdrawal compared with pre-operation was deemed to be due to cold allodynia.

1.2.3. Behavioral Tests for Warm Allodynia

The tests for warm allodynia were performed as those for cold allodynia described above except for using warm water (40° C.). Where the faster withdrawal compared with pre-operation was significantly determined, it was deemed to be due to warm allodynia.

In behavioral tests described above, the statistically significant avoidance responses after nerve injury were determined to be resulting from pain induction.

2. Drug Administration

To verify analgesic effects of FVIA and MVIIA on chronic neuropathy, the behavioral tests were carried out during 14 days after nerve injury operation and rats exhibiting pain induction were selected for drug administration.

Drugs were suspended in a physiological saline and intrathecally administered as follows. Rats were slightly anesthetized using enflurane and administered with drugs using 25-µl Hamilton syringe with 30-gauge needle. The drugs were injected to the subarachnoid space via the dura mater between L5 and L6 spinal nerves. The dosages of drugs were 6.5, 20, 65 or 200 ng/kg. The analgesic effects on mechanical allodynia were monitored with a time interval of 15 min by 1 hr post-injection, with a time interval of 30 min by 3 hr post-injection, at 5 hr post-injection and at 24 hr post-injection, respectively. The analgesic effects on cold and warm allodynia were examined at 1 hr, 3 hr, 5 hr and 24 hr after injection.

Measurement of Mean Arterial Pressure

Sprague-Dawley male rats weighed 150-200 g were housed in colony cages and were given a standard laboratory chow and water ad libitum. They were maintained under a 12 hr/12 hr light-dark cycle, temperature (22±3° C.) and humidity (40-60%). All operations were conducted under anesthetization with isoflurane. Catheter (PE-10) was inserted to the femoral artery and filled with a physiological saline, followed by connecting to a patient monitoring apparatus (Philips MP30, Intellivue). The peptides MVIIA or FVIA were administered into lateral tail veins of rats. For electrocardiogram, stainless electrodes were placed to two knees and portions beneath skin of the hind leg.

Statistical Analysis

All experimental data are presented as mean±standard error mean (SEM). The drug effects on neuropathic pains are compared and analyzed with one-way repeated measured ANOVA and Bonferroni t-test. A p-value less than 0.05 was considered statistically significant. The antiallodynic effect was evaluated by the increment of the withdrawal threshold after the drug treatment and expressed as percentage of maximal possible effect (% MPE): % MPE=100×[(withdrawal threshold$_{post\text{-}treatment}$)−(withdrawal threshold$_{post\text{-}operation}$)/(withdrawal threshold$_{pre\text{-}operation}$)−(withdrawal threshold$_{post\text{-}operation}$)].

Results

Conopeptide Isolation

Our group characterized several conopeptide using biochemical methods (venom extraction and HPLC). Concurrently, we used DNA cloning from *Conus Flavidus* venom duct mRNA or gDNA to obtain additional conopeptides. About 50 conopeptides were characterized by above methods. These included O-superfamily, A-superfamily, M-superfamily and the other superfamily [1].

In the characterized sequences, FVIA shows high sequence homology with well-known ω-conopeptide MVIIA (76%) and also has conserved residue $Tyr^{13}$, $Lys^2$, and $Arg^{10}$ (Table 1). Only 6 residues are different in whole sequence. The cDNA sequence of FVIA was identified as SEQ ID NO:4.

TABLE 1

Comparison of primary sequences of ω-conotoxin FVIA and other N-type calcium channel blockers

| Name | Amino acid sequence | Homology |
|---|---|---|
| FVIA (SEQ ID NO: 1) | C KGTGKS C SRIAYN CC TGS C R SGK C-NH$_2$ | — |
| MVIIA (SEQ ID NO: 5) | C KGKGAK C SRLMYD CC TGS C R SGK C-NH$_2$ | 76% |
| CVIA (SEQ ID NO: 9) | C KSTGAS C RRTSYN CC TGS C R SGR C-NH$_2$ | 72% |
| GVIA (SEQ ID NO: 10) | C KSPGSS C SPTSYN CC R S C NPYTKR CY-NH$_2$ | 52% |
| CVID (SEQ ID NO: 11) | C KSKGAK C SKLMYD CC SGS C SGTVGR C-NH$_2$ | 48% |

Peptide Synthesis

Figure 1B:
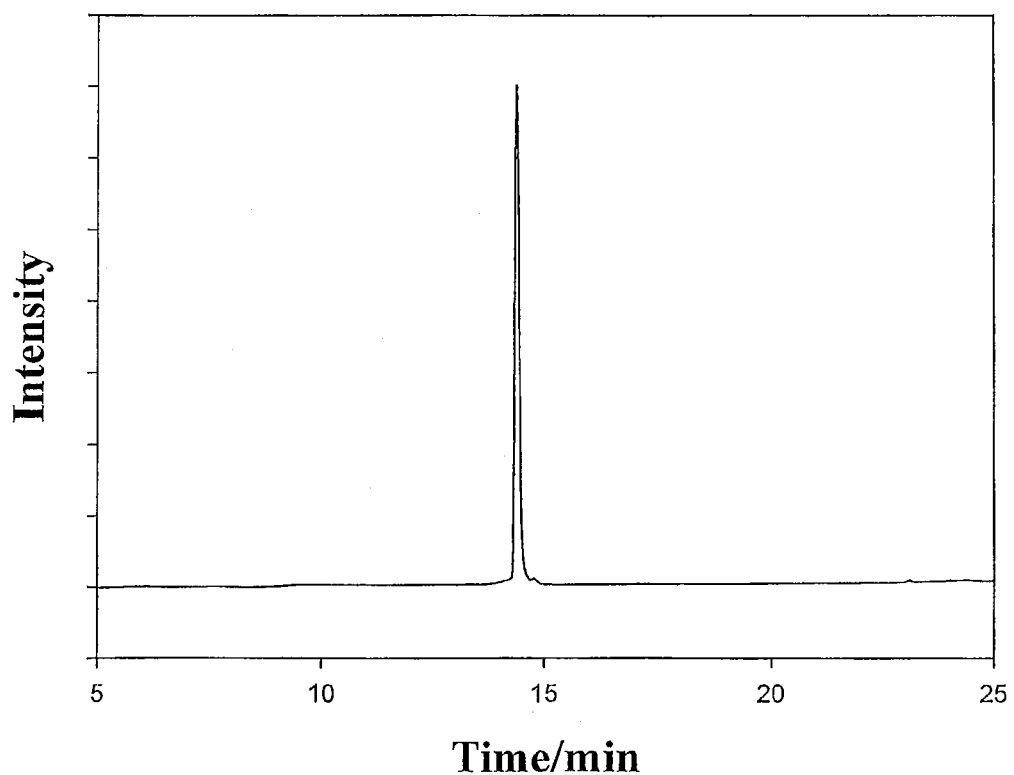

Solid phase chemical synthesis of FVIA was undertaken to provide an abundant supply of peptide and synthesis of protected linear peptides proceeded smoothly. After TFA cleavage, the linear precursor of FVIA from which all protected group had been removed was extracted from 20% acetic acid. Air oxidation of the crude peptides afforded peptides having proper disulfide bond pairings as the major products, which were purified by ion exchange chromatography and reverse phase HPLC. FVIA is strongly basic peptide with net charge +5 at neutral pH, so we used CM-cellulose CM52 as cation exchange chromatography using NH$_4$OAc buffer gradient as eluent. The final purified products were confirmed by analytical HPLC, amino acid analysis and MALDI-TOF-MS measurements (FIG. 1).

CD Measurement

Figure 2A:
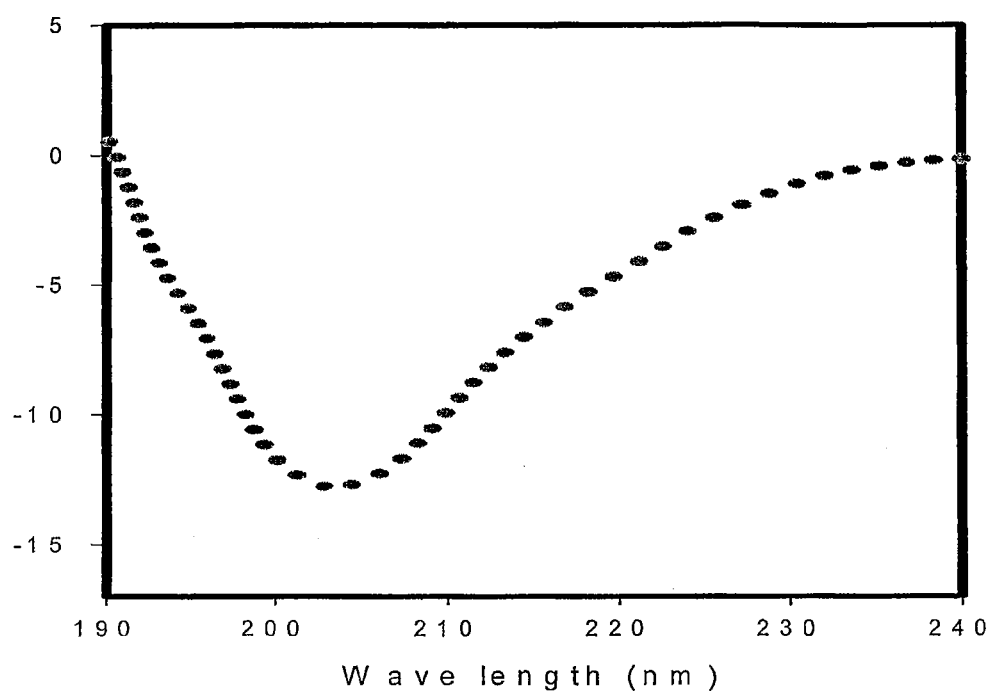
FIGS. 2A and 2B represent CD spectra of FVIA (FIG. 2A) and its analogues (FIG. 2B). FVIA have β-turn structure or antiparallel β-sheet on the basis of secondary structure spectra for five major secondary structures, including α-helix, antiparallel β-sheet, parallel β-sheet, β-turn and random. The secondary structure of FVIA is formed properly by oxidative folding [18].
Figure 2B:
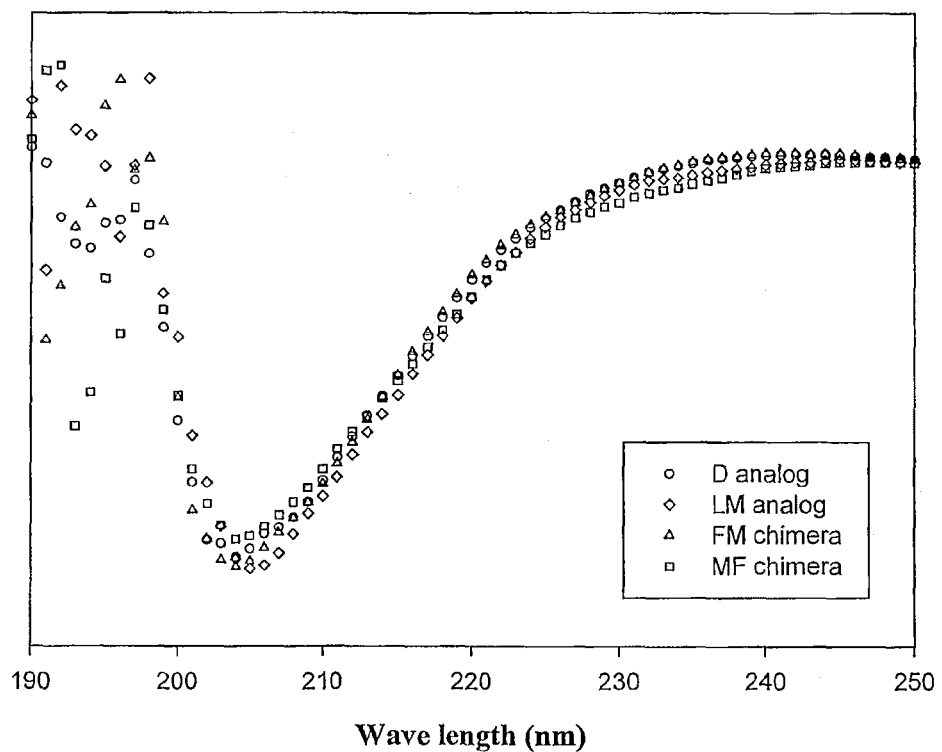

The CD spectrum of FVIA shows two minima at around 205 nm (FIG. 2A). It is expected that FVIA have β-turn structure or antiparallel β-sheet on basis of secondary structure spectra for five major secondary structures, including α-helix, antiparallel β-sheet, parallel β-sheet, β-turn and random [18]. It proved that the secondary structure of FVIA is formed properly by oxidative folding [19]. CD spectra for FVIA analogues, chimera-FMFF, chimera-MFMM, FVIA [N14D] and FVIA[I11L, A12M] showed that the secondary structures of them were almost the same as that for FVIA, demonstrating that the difference in activities of them are attributed to the difference in amino acid residues (FIG. 2B).

Electrophysiology

Figure 3:
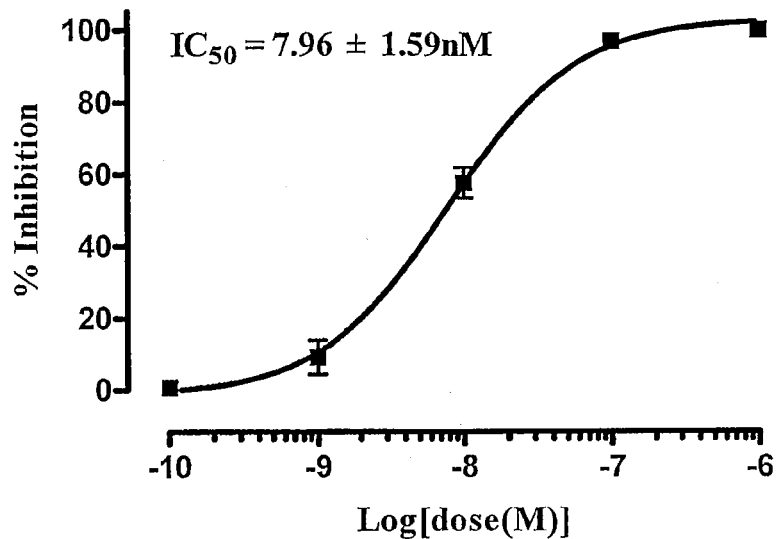
FIG. 3 is dose-inhibition curves of MVIIA (panel A) and FVIA (panel B). The range of doses is 1 μM from 0.1 nM. Both graphs show curves with sigmoid shape and is saturated with 0.1 μM. $IC_{50}$ values of each peptide were 7.96±1.59 nM and 11.5±1.4 nM, respectively.
Figure 3:
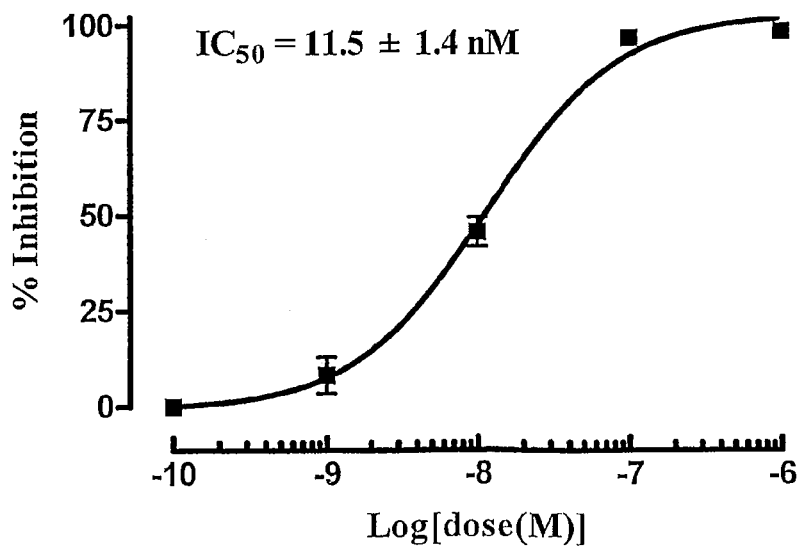

To investigate in vitro activity of ω-conotoxins, electrophysiology studies were performed [20]. $IC_{50}$ values mean the potencies of ω-conotoxins and are calculated from dose-inhibition (response) curve. The range of doses is 1 μM from 0.1 nM. Synthetic MVIIA and FVIA blocked human N-type calcium channel expressed in human embryonic kidney cells with similar potency (FIG. 3). Both graph show curve with sigmoid shape and is saturated with 0.1 μM. $IC_{50}$ values of each peptide were 7.96±1.59 nM and 11.5±1.4 nM, respectively.

Second experiment is current-voltage measurement of ω-conotoxins. The mechanism of channel blocker can be classified to pore blocking and gate modifying actions. It well known that ω-conotoxins, including MVIIA, are pore blocker and bind to the vestibubule of N-type calcium channel pore region. FVIA also show the curve inhibition without the horizontal curve shift (FIG. 4) [42].

Figure 5:
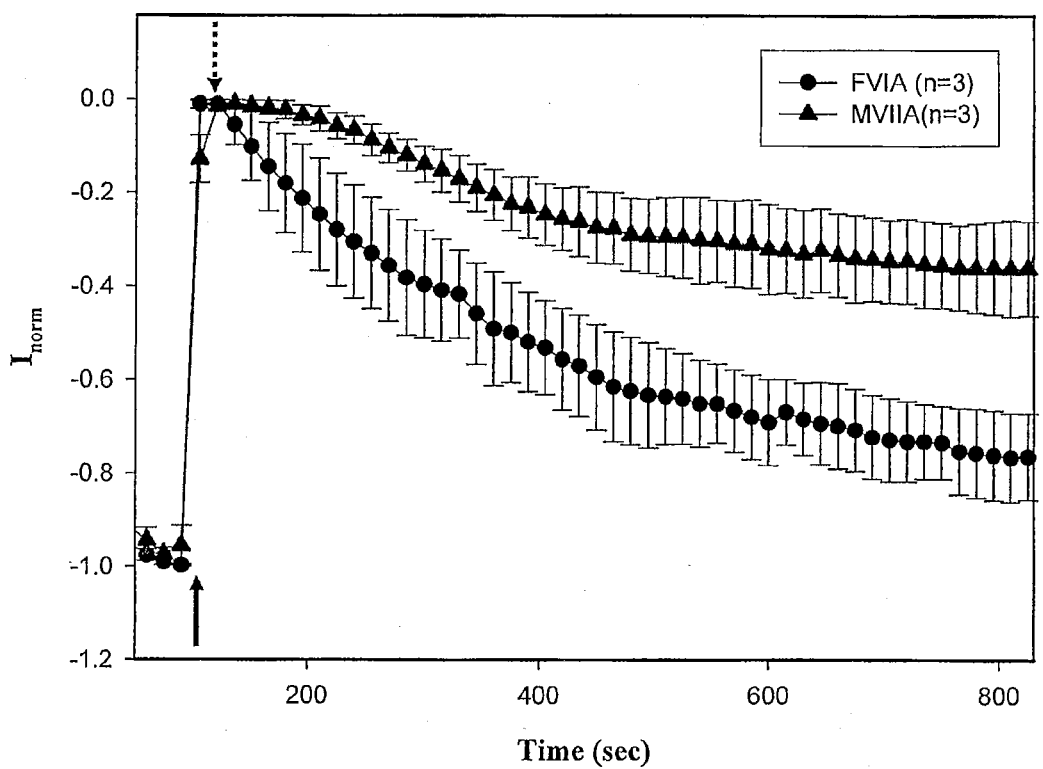
FIG. 5 is recovery curves of FVIA and MVIIA. Solid line arrow indicates 1 μM conotoxins application and broken line arrow indicates wash-out with buffers.

Finally, we check the recovery from the binding to the N-type VSCC. The toxins were washed out when the blocking were saturated with 1 μM concentration. Although the blocking of FVIA is exhibited faster than MVIIA, FVIA shows better dissociation comparing MVIIA washout (FIG. 5).

NMR Analysis

The two-dimensional $^1H$ NMR spectra of ω-conotoxins FVIA were assigned using standard protocols [43]. Peaks were well dispersed and there was some overlap in loop 2 and 4 (Table 2). Identification of the amino acid spin system was based on scalar coupling patterns observed in DQF-COSY and TOCSY experiments, complemented by the results of NOESY measurements. The identified spin systems were ordered along the primary structure of FVIA through inter-residue sequential NOEs observed on the NOESY spectrum. Table 3 shows the chemical shift of NOESY spectrum.

TABLE 2

Chemical shifts of FVIA at 298 K and pH 3.5

| | Chemical shift (p.p.m) | | | |
|---|---|---|---|---|
| Residues | NH | $C_\alpha H$ | $C_\beta H$ | others |
| Cys1 | — | 4.503 | 3.095, 3.273 | — |
| Lys2 | 9.101 | 4.503 | 1.930, 1.711 | $C_\gamma H$ 1.406 $C_\delta H$ 1.555 |
| Gly3 | 8.770 | 3.827, 4.048 | — | — |
| Thr4 | 8.280 | 3.713 | 3.934 | $C_\gamma H$ 1.235 |
| Gly5 | 9.260 | 3.626, 4.344 | — | — |
| Lys6 | 7.664 | 4.503 | 2.077, 1.901 | $C_\gamma H$ 1.478, $C_\delta H$ 1.627 |
| Ser7 | 8.406 | 4.866 | 3.900, 3.946 | — |
| Cys8 | 8.166 | 4.970 | 3.127, 3.275 | — |
| Ser9 | 8.350 | 4.675 | 4.037, 3.821 | — |
| Arg10 | 8.610 | 4.105 | 1.665 | $C_\gamma H$ 1.860 |
| Ile11 | 7.618 | 4.184 | 1.888 | $C_\gamma H2$ 1.352, 1.159; $C_\gamma H3$ 0.085 |
| Ala12 | 7.698 | 4.355 | 1.233 | — |
| Tyr13 | 7.846 | 4.628 | 3.164 | C2, 6H 6.852; C3, 5H 7.129 |
| Asn14 | 8.257 | 4.779 | 2.672, 2.832 | — |
| Cys15 | 8.313 | 4.960 | 2.556, 3.251 | — |
| Cys16 | 9.590 | 4.412 | 2.921, 3.253 | — |
| Thr17 | 8.441 | 4.472 | 4.072 | $C_\gamma H$ 1.119 |
| Gly18 | 8.360 | 3.820, 4.097 | — | — |
| Ser19 | 8.201 | 4.722 | 3.706, 3.786 | — |

TABLE 2-continued

Chemical shifts of FVIA at 298 K and pH 3.5

| | Chemical shift (p.p.m) | | | |
|---|---|---|---|---|
| Residues | NH | $C_\alpha H$ | $C_\beta H$ | others |
| Cys20 | 8.725 | 4.711 | 2.829, 2.899 | — |
| Arg21 | 8.622 | 4.644 | 1.841 | $C_\gamma H$ 1.634, 1.544 |
| Ser22 | 9.317 | 4.047 | 3.900, 4.127 | — |
| Gly23 | 8.224 | 4.152, 3.786 | — | — |
| Lys24 | 7.768 | 5.120 | 1.632, 1.520 | $C_\gamma H$ 1.260; $C_\delta H$ 1.357 |
| Cys25 | 8.712 | 4.859 | 3.023, 3.228 | — |
| amide | — | — | — | $NH_2$ 8.441 |

Figure 6:
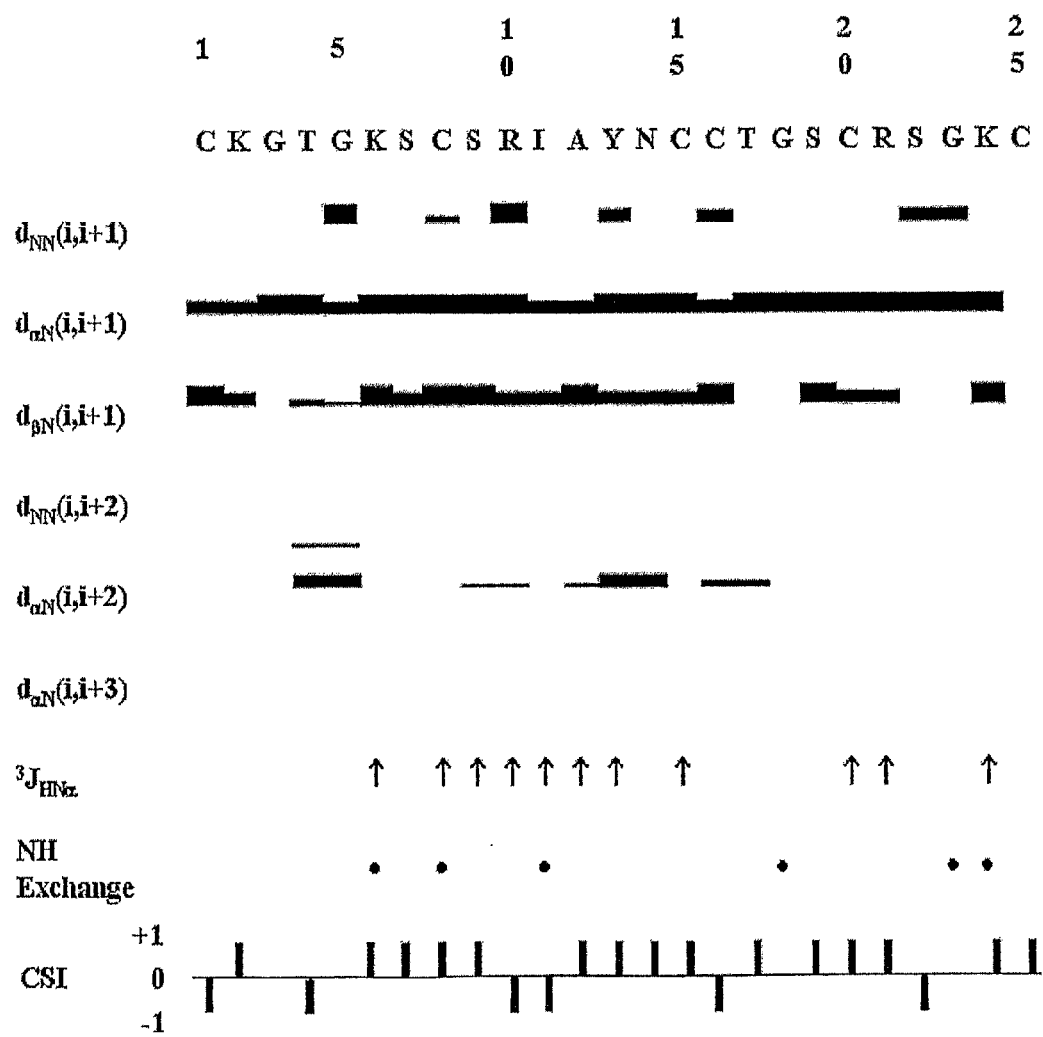
FIG. 6 represents summary of the sequential and medium range NOE connectionvities, $^3J_{NH-CoH}$ coupling, and slowly exchanging backbone NH protons observed in FVIA (SEQ ID NO: 1). These structural parameters were used for the sequence specific assignments and identification of secondary structure elements in ω-conotoxin FVIA. The NOEs are classified into strong, medium, weak, and very weak, according to the height of the filled bars. The values of the $^3J_{NH-Co}$ coupling constants are indicated by filled circle (≥8 Hz) and opened circle (≤5.5 Hz) symbols. The chemical shift index is indicated by a ternary index with values of −1, 0, and +1. The values of −1 and +1 indicated a shift deviation from the random-coil values of greater than 0.1 p.p.m. upfield and downfield, respectively, and those within the range of random-coil values are indicated 0.
Figure 7A:
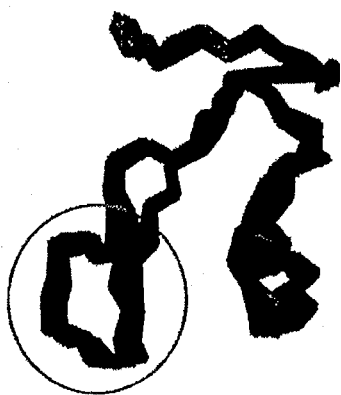
FIGS. 7A and 7B represent (panel A) comparison between FVIA (SEQ ID NO: 1) and MVIIA (SEQ ID NO: 5) backbone structure and (panel B) the position of effective residues of FVIA and MVIIA in reversibility.
Figure 7A:
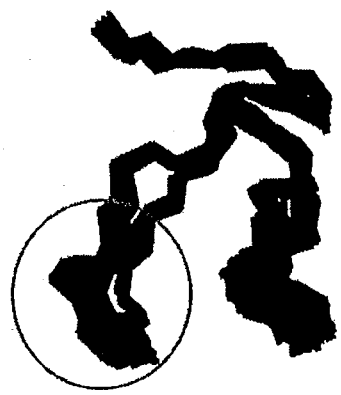
Figure 7B:
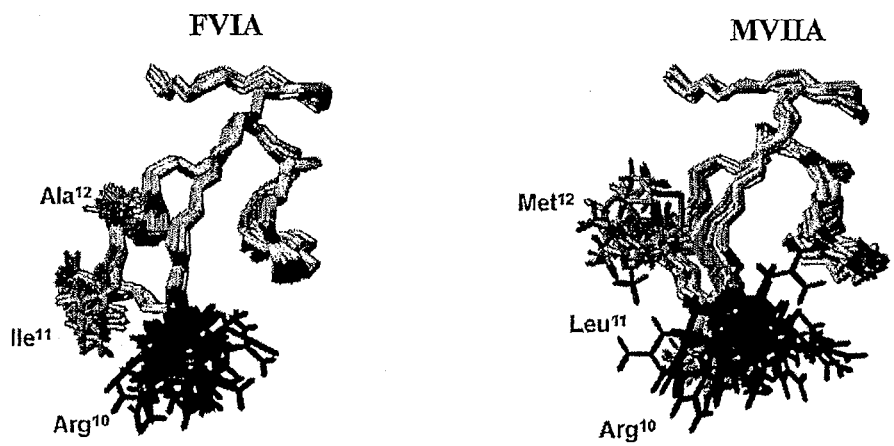

As summarized in FIG. 6, FVIA contains three short β-strands comprised of residues 6-8, 21 and 24, which are arranged in antiparallel fashion with several turns. The extent of the β-strands and their relative orientation in the β-sheet structure were determined using standard criteria: large $^3J_{NH-C\alpha}$ coupling constants (Lys$^6$, Cys$^8$, Ser$^9$, Arg$^{10}$, Ile$^{11}$, Ala$^{12}$, Tyr$^{13}$, Cys$^{15}$, Cys$^{20}$, Arg$^{21}$, Lys$^{24}$), strong sequential $d_{\alpha N}$, interstrand NH—NH and NH—$C^\alpha H$ connectivities, and slowly exchanging amide protons (Lys$^6$, Cys$^8$, Ile$^{11}$, Gly$^{18}$, Gly$^{23}$, Arg$^{21}$ and Lys$^{24}$). These criteria enabled discrimination of the peripheral and central strands within the β-sheet.

Calculation of the Solution Structure of FVIA

We used a total of 317 NMR experimental constraints to calculate the three-dimensional structure of FVIA, including 301 experimental distance constraints and 16 dihedral angle constraints, which correspond to an average of 12.68 constraints per residue. Of the 285 distance constraints, there were 128 intraresidue, 156 interresidue NOE distance constraints, 8 hydrogen bond constraints determined from hydrogen-deuterium exchange-out experiments, and 9 disulfide bond constraints. The 3 distance constraints related to hydrogen bonds are: Gly$^5$ (NH)-Cys$^{25}$ (CO), Lys$^6$ (NH)-Gly$^3$ (CO), Cys$^8$ (NH)-Gly$^{23}$ (CO), Ile$^{11}$ (NH)-Ser$^9$ (OH), Gly$^{18}$ (NH)-Cys$^{15}$ (CO), Arg$^{21}$ (CO)-Lys$^{24}$ (NH), and Arg$^{21}$ (CO)-Lys$^{24}$ (NH).

We carried out the simulated annealing calculations starting with 100 random FVIA structures, and selected 20 final structures that were in good agreement with the NMR experimental constraints, for which the NOE distance and torsion angle violations were smaller than 0.3 Å and 3°, respectively. Statistics for the converged structures were evaluated in terms of structural parameter (Table 3).

TABLE 3

Structural statistics for the 20 lowest energy structures

| | |
|---|---|
| RMS deviations from experimental distance restraints (Å)$^a$ (301) | 0.037 ± 0.008 |
| RMS deviations from experimental dihedral angle restraints (deg.)$^a$ (17) | 0.037 ± 0.008 |
| Energetic statistics (kcal/mol)$^b$ | |
| $F_{NOE}$ | 0.245 ± 0.165 |
| $F_{tor}$ | 5.021 ± 0.359 |
| $F_{repel}$ | 4.109 ± 1.475 |
| $E_{L-J}$ | −54.690 ± 6.728 |
| RMS deviations from idealized geometry | |
| Bonds (Å) | 0.0033 ± 0.0001 |
| Angles (deg) | 0.558 ± 0.02 |
| Impropers (deg) | 0.443 ± 0.0156 |

TABLE 3-continued

Structural statistics for the 20 lowest energy structures

Ramanchandran analysis (residues 2-30)[c]

| | |
|---|---|
| Most favored (%) | 42.9 |
| Additional allowed (%) | 56.3 |
| Generously allowed (%) | 0.8 |
| Disallowed region (%) | 0.0 |

Average pairwise RMS difference (Å)[c]

| | |
|---|---|
| Backbone (residues 2-30) | 0.47 ± 0.10 |
| All heavy atoms (residues 2-30) | 1.36 ± 0.21 |

[a]The number of each experimental constraint used in the calculations is given in parentheses.
[b]$F_{NOE}$, $F_{tor}$, and $F_{repel}$ are energies related to the NOE violations, the torsion angle violations and van der Waals repulsion term, respectively. The values of the force constants used for these terms are the standard values as depicted in the X-PLOR 3.1 Manual. $E_{L-J}$ is the Lennard-Jones van der Waals energy calculated with the CHARMM empirical energy function, which was not included in the simulated annealing calculation.
[c]The program PROCHECK-NMR was used to assess the stereochemical quality of the structures.

The deviations from the idealized covalent geometry were very small, and the Lennard-Jones van der Waals energy was large and negative, indicating there to be no distortions or non-bonded bad contacts in the conserved structures. The atomic RMS deviation about the mean coordinate positions for total sequence was 0.47±0.10 Å for the backbone atoms (N, $C_\alpha$, C) and 1.36±0.21 Å for all heavy atoms. The backbone structures for total sequence were well defined in whole sequence; Ramachandran analysis showed the backbone dihedral angles to fall either within the β-sheet region or in generally allowed regions.

Molecular Structure of FVIA

The molecular structure of FVIA consists of a triple-stranded antiparallel β-sheet and four chain reversals. The overall β-sheet topology of FVIA is +2x, −1, which is frequently associated with toxic and inhibitory peptides having an "inhibitory cysteine knot" fold [45]. The three β-strands are formed by residues Ser[7]-Cys[8] (β-strand I), Arg[21] (β-strand II) and Gly[23]-Lys[24] (β-strand III), with β-strand I tethered to β-strand II by a disulfide bond (Cys[8]-Cys[20]) and interacting with the central β-strand III in antiparallel fashion at an angle of about 45°. The first chain reversal occurs at residue Gly[3]-Lys[6], which form a type II β-turn. The second and third reversals occur at residues Ser[9]-Ala[12] and Cys[15]-Gly[18], which respectively form a type IV β-turn and a type I β-turn. The final reversal occurs at resides Arg[21]-Lys[24] and forms a β-hairpin turn (a type IV β-turn) that reverses the direction of the backbone between β-strands II and III.

Construction of FVIA Site Specific Substituted Analogues, Calcium Channel Inhibition and Recovery Analysis To verify portions and residues of FIVA crucial for activities and recovery, site-specific substituted analogues were prepared as indicated in Table 4.

TABLE 4

FVIA analogues

| Peptides | Amino acid sequence |
|---|---|
| FVIA (SEQ ID NO: 1) | CKGTG KSCSR IAYNC CTGSC RSGKC-NH$_2$ |
| MVIIA (SEQ ID NO: 5) | CKGKG AKCSR LMYDC CTGSC RSGKC-NH$_2$ |
| Chimera-FMFF (SEQ ID NO: 12) | CKGTG KSCSR LMYDC CTGSC RSGKC-NH$_2$ |
| Chimera-MFMM (SEQ ID NO: 17) | CKGKG AKCSR IAYNC CTGSC RSGKC-NH$_2$ |

TABLE 4-continued

FVIA analogues

| Peptides | Amino acid sequence |
|---|---|
| FVIA[N14D] (SEQ ID NO: 3) | CKGTG KSCSR IAYDC CTGSC RSGKC-NH$_2$ |
| FVIA[I11L, A12M] (SEQ ID NO: 13) | CKGTG KSCSR LMYNC CTGSC RSGKC-NH$_2$ |

FVIA analogues were analyzed to reveal their calcium channel blocking potentials and recovery. For this experiment, 30 nM FVIA analogues were used. The analysis results are summarized in Table 5.

TABLE 5

Calcium channel blocking activities and recovery of FVIA analogues

| Peptides | Blocking activity (%) | Recovery (%) |
|---|---|---|
| FVIA (SEQ ID NO: 1) | 94.7 ± 2.1 | 69.7 ± 6.5 |
| MVIIA (SEQ ID NO: 5) | 81.5 ± 2.4 | 39.5 ± 6.8 |
| Chimera-FMFF (SEQ ID NO: 12) | 84.2 ± 2.9 | 24.7 ± 1.1 |
| Chimera-MFMM (SEQ ID NO: 17) | 93.4 ± 1.9 | 70.3 ± 10.6 |
| FVIA[N14D] (SEQ ID NO: 3) | 54.4 ± 8.7 | 87.7 ± 7.8 |
| FVIA[I11L, A12M] (SEQ ID NO: 13) | 84.3 ± 4.7 | 39.0 ± 5.7 |

As understood in Table 5, the chimera-MFMM, which has the backbone of the conventional conotoxin MVIIA substituted by FVIA residues at amino acids 11-15, exhibits not only significant calcium channel blocking activity but also almost 2-fold higher recovery potential than unmodified MVIIA. Therefore, it could be appreciated that the amino acid residues spanning 11-15 positions are responsible for dramatically enhanced reversibility of FVIA.

For obtaining more information, Ile and Ala residues positioned at amino acids 11 and 12 of FVIA, respectively were mutated to Leu and Met, respectively to prepare FVIA [I11L, A12M]. This analogue was analyzed to have calcium channel blocking activity similar to FVIA but to show significantly reduced reversibility. In this regard, it could be understood that Ile and Ala residues positioned at amino acids 11 and 12 of FVIA are crucial for recovery, i.e., reversibility.

Animal Tests for Analgesic Effect

The present peptide FVIA was tested to exhibit analgesic effect in mice.

Figure 8A:
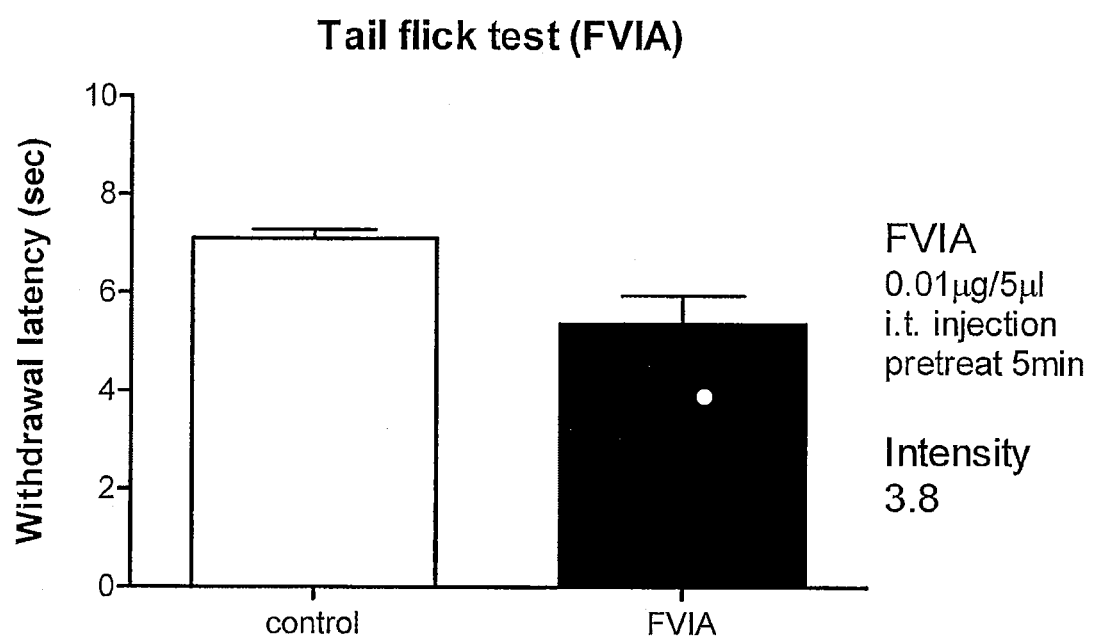
FIGS. 8A and 8B represent analgesic effects of FVIA examined by tail flick test (panel A) and plantar test (panel B). The time that withdrawal behaviors were observed was recorded.
Figure 8B:
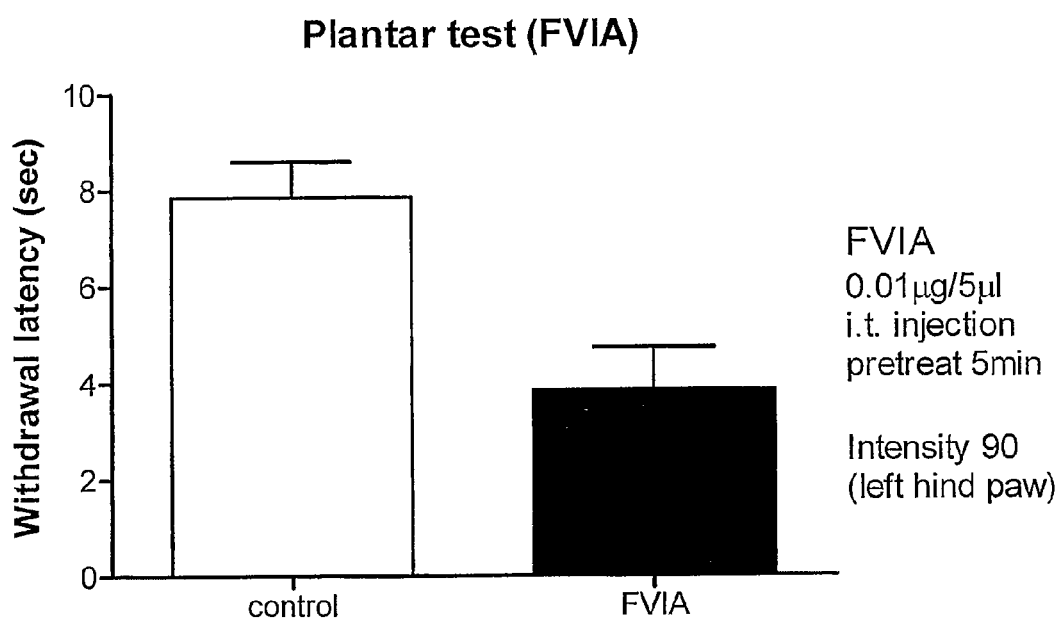

As shown in FIGS. 8A and 8B for tail-flick test and plantar test, the FVIA peptide (0.01 μg/5 μl) administered to mice was not effective in increasing withdrawal latency compared with control.

Figure 9A:
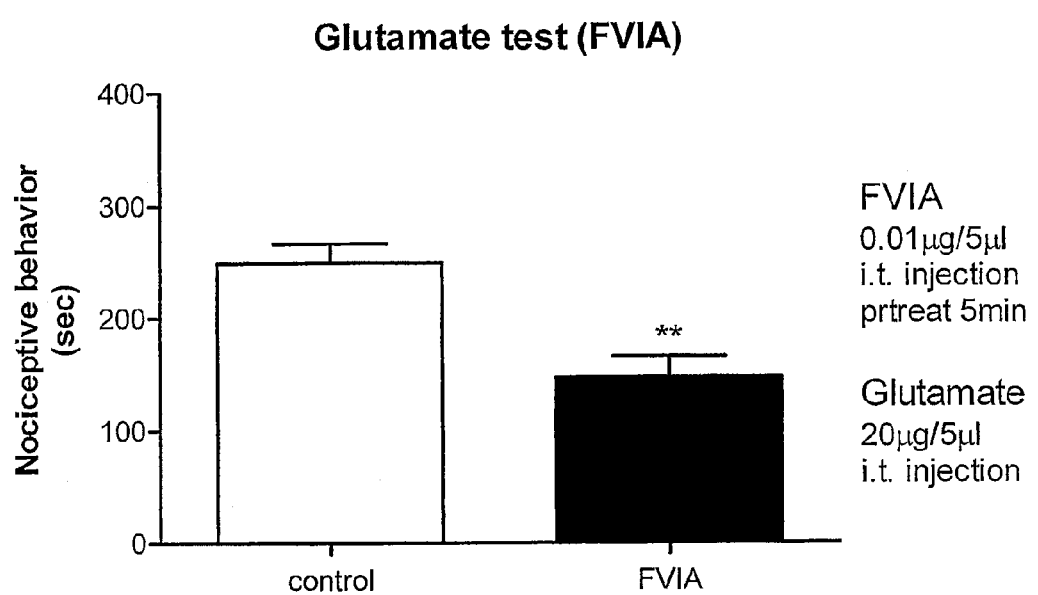
FIGS. 9A, 9B and 9C represent analgesic effects of FVIA on pains induced by glutamate (panel A), substance P (panel B) or acetic acid (panel C). Bar, standard error of mean.; *, P value compared with control (*P<0.05, P<0.01, *P<0.001).
Figure 9B:
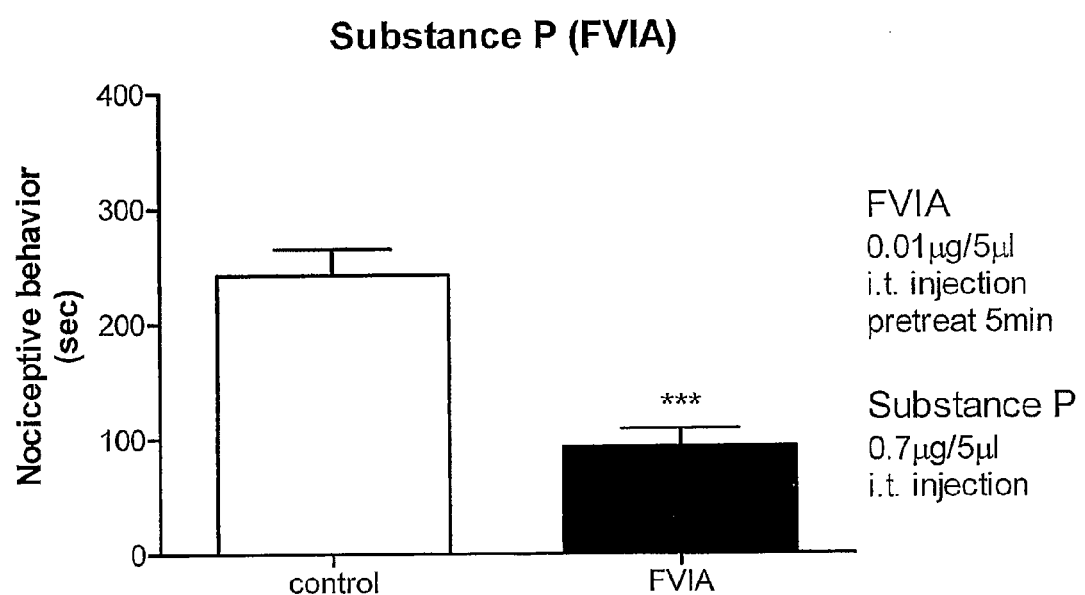

The control mice injected with either glutamate (20 μg/5 μl) or substance P (0.7 μg/5 μl) were observed to elicit acute behavioral responses such as licking, biting or scratching for 30 min, as demonstrated in FIGS. 9A and 9B. In contrast, the mice administered with FVIA were observed to show significantly decreased cumulative pain response rate.

Figure 9C:
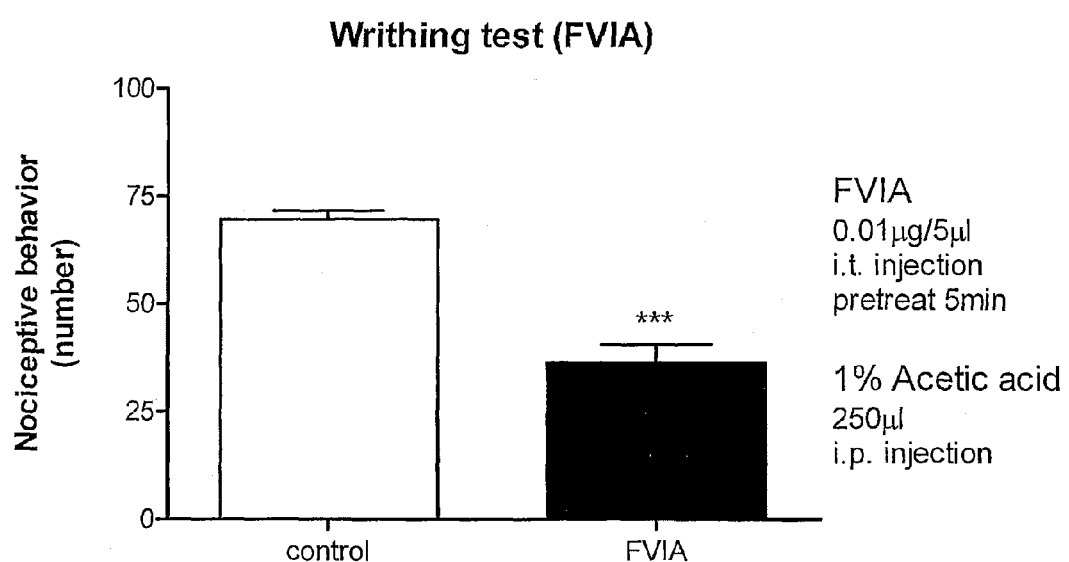

For the control mice administered with a physiological saline, the intraperitoneal injection of 250 μl of 1.0% acetic acid induced about 70 writhing responses. By contrast, the count of writhing responses in the mice administered with FVIA was significantly decreased, as represented in FIG. 9C.

Figure 10A:
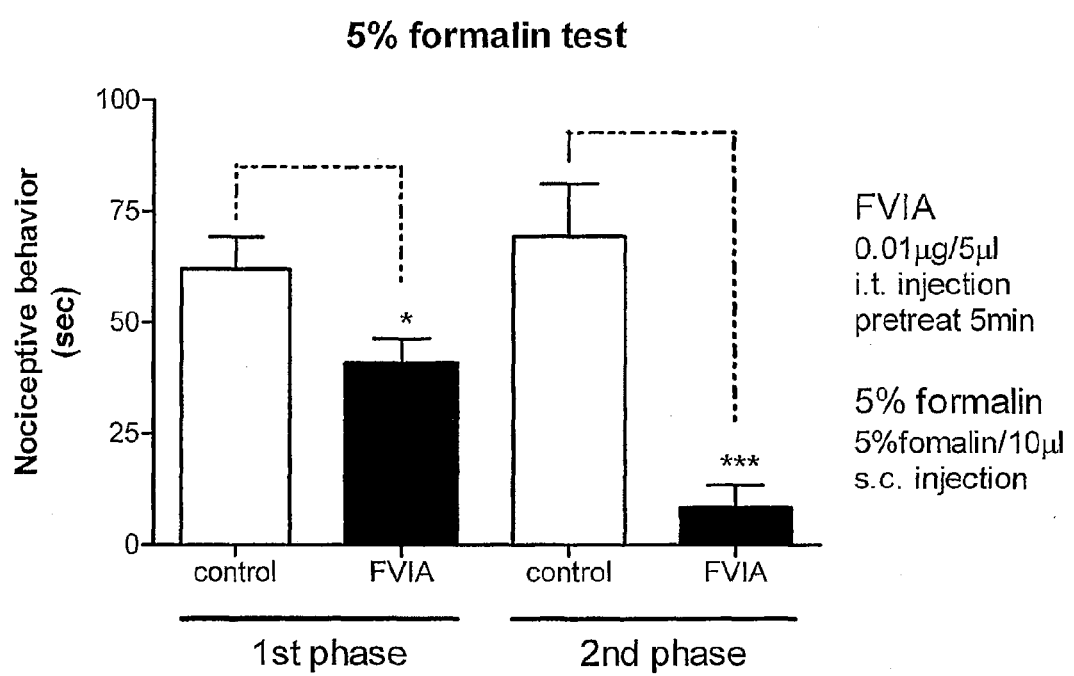
FIGS. 10A and 10B represent analgesic effects of FVIA on pains induced by 5% formalin injection.

As shown in FIG. 10A, for mice subcutaneously injected with 10 µl of 5% formalin, there were two distinct phases: the first phase which appeared immediately after formalin injection and lasted 5 min, and the second phase which appeared about 20 min after formalin administration and lasted 20-40 min. The mice were observed to show pain behavior activities such as licking, biting, scratching or shaking. In contrast to these, the mice administered with FVIA were observed to show significantly decreased cumulative pain response rate in both the first phase and the second phase. Furthermore, it was revealed that FVIA was much more effective in the second phase than the first phase.

Figure 10B:
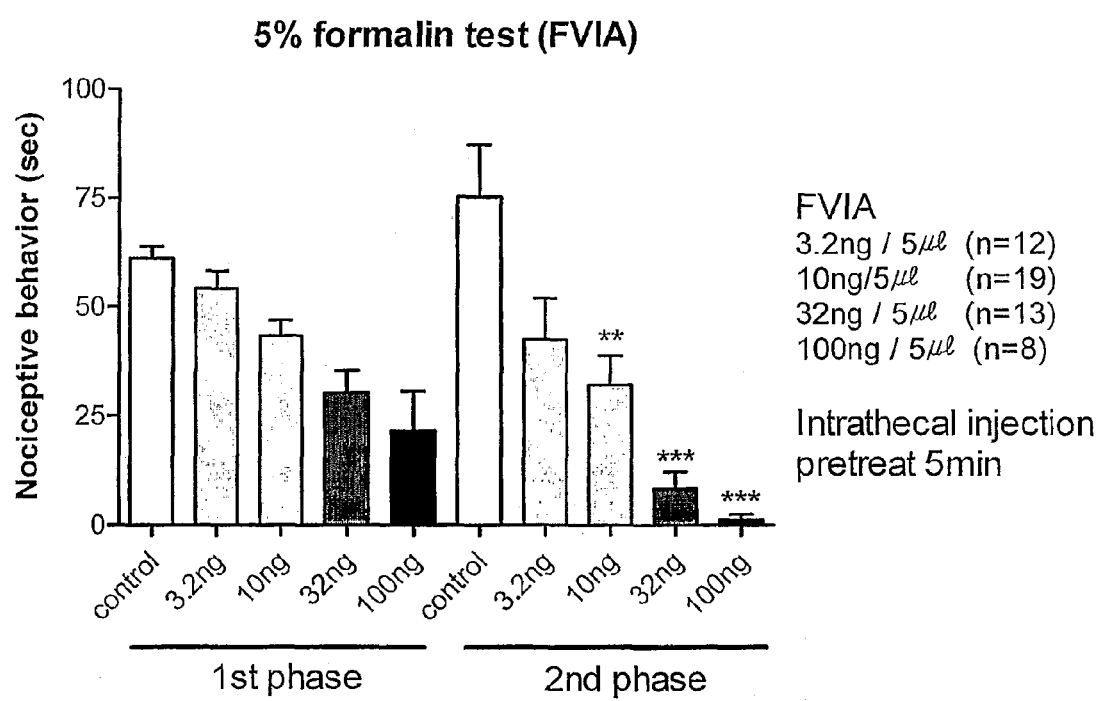

The present peptide FVIA was elucidated to exert analgesic effect in a dose-dependent manner, as represented in FIG. 10B. The analgesic effect of FVIA became increased as the concentration of FVIA administered was elevated (3.2 ng/5 µl, 10 ng/5 µl, 32 ng/5 µl and 100 ng/5 µl). Interestingly, 100 ng of FVIA administered completely prevented pain behaviors in the second phase.

These results described above led us to reason that the FVIA peptide successfully exhibits analgesic effect in animals.

Analgesic Effects on Neuropathic Pains

We produced two types of neuropathy model: animal models with injured L5 and L6 spinal nerves; and animal models with injured S1 and S2 spinal nerves. The animal models with injured nerves were observed to exhibit neuropathic pain and allodynia.

Figure 11A:
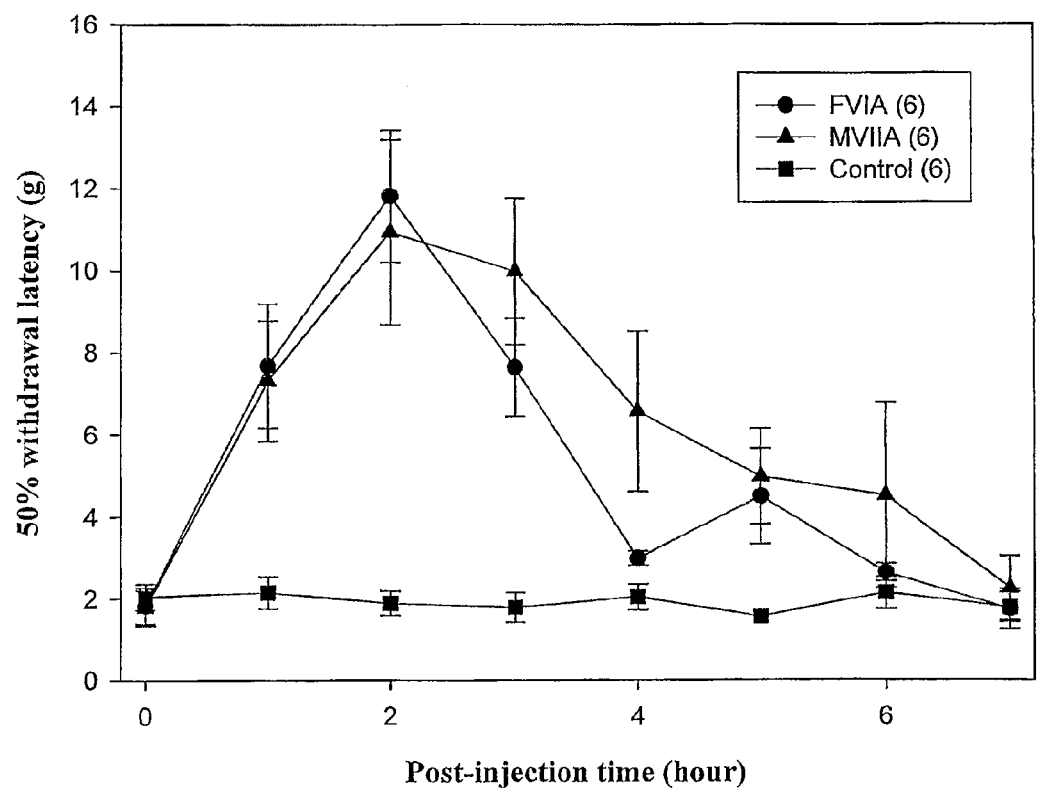
FIGS. 11A and 11B represent analgesic effects of FVIA in neuropathic pain models with injured leg nerves. 0.1 ng of FVIA was intrathecally injected.
Figure 11B:
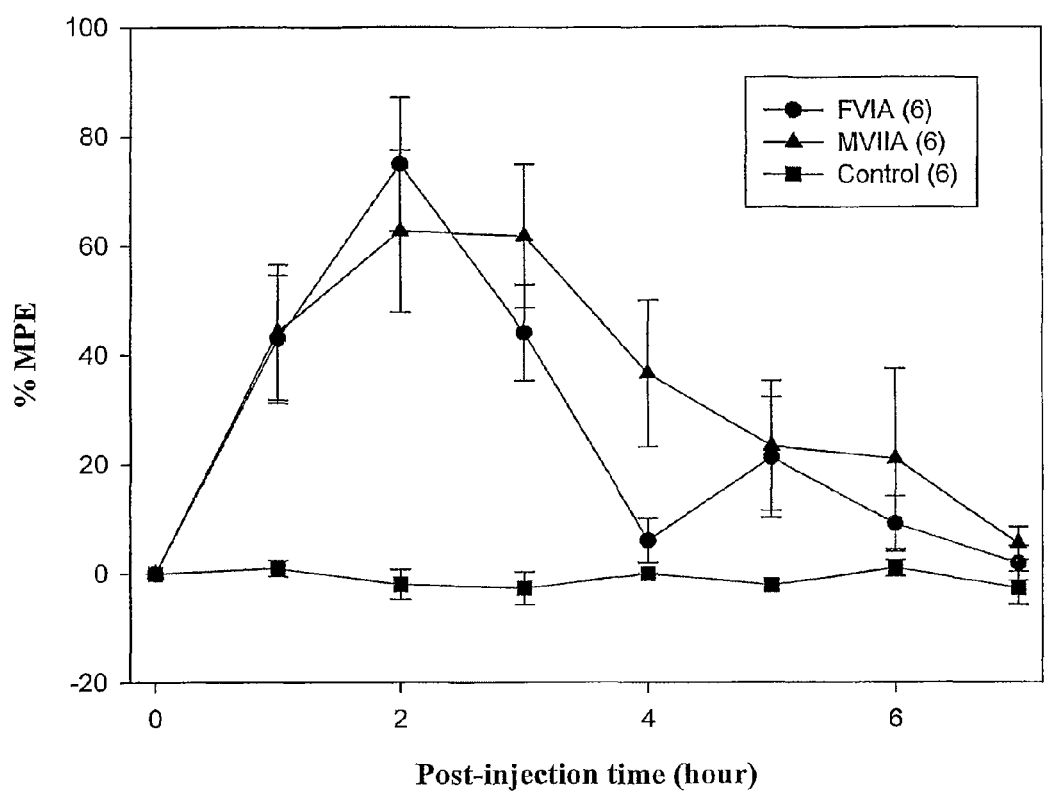
Figure 12A:
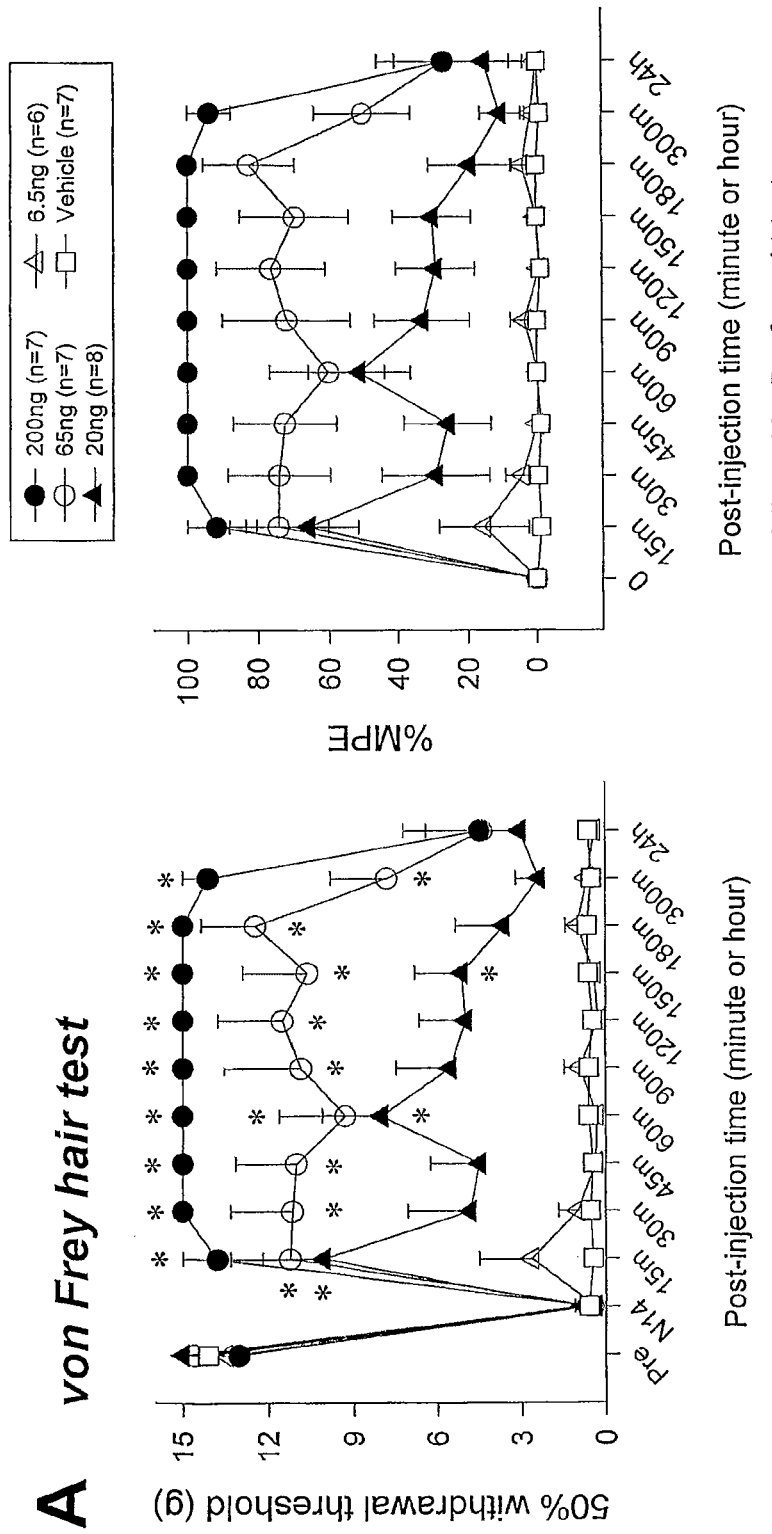
FIGS. 12A, 12B and 12C represent analgesic effects of FVIA in neuropathic pain models with injured tail nerves. After 14 days of nerve injury operations, analgesic effects of FVIA were accessed on mechanical allodynia (panel A), cold allodynia (panel B) and warm allodynia (panel C). The symbol * was indicated if P value is less than 0.05 compared with values of FVIA pre-injection. The right graphs are % MPE graphs corresponding to the results of FIGS. 12A-12C.
Figure 12B:
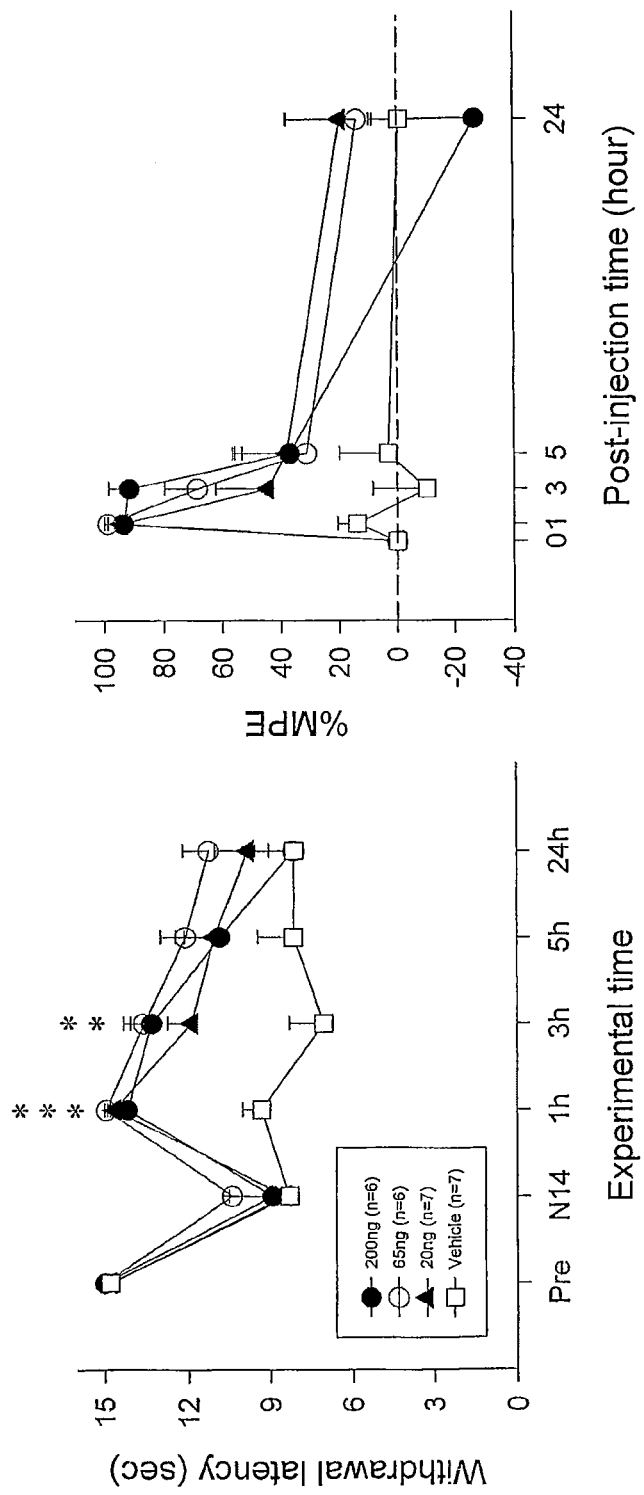
Figure 12C:
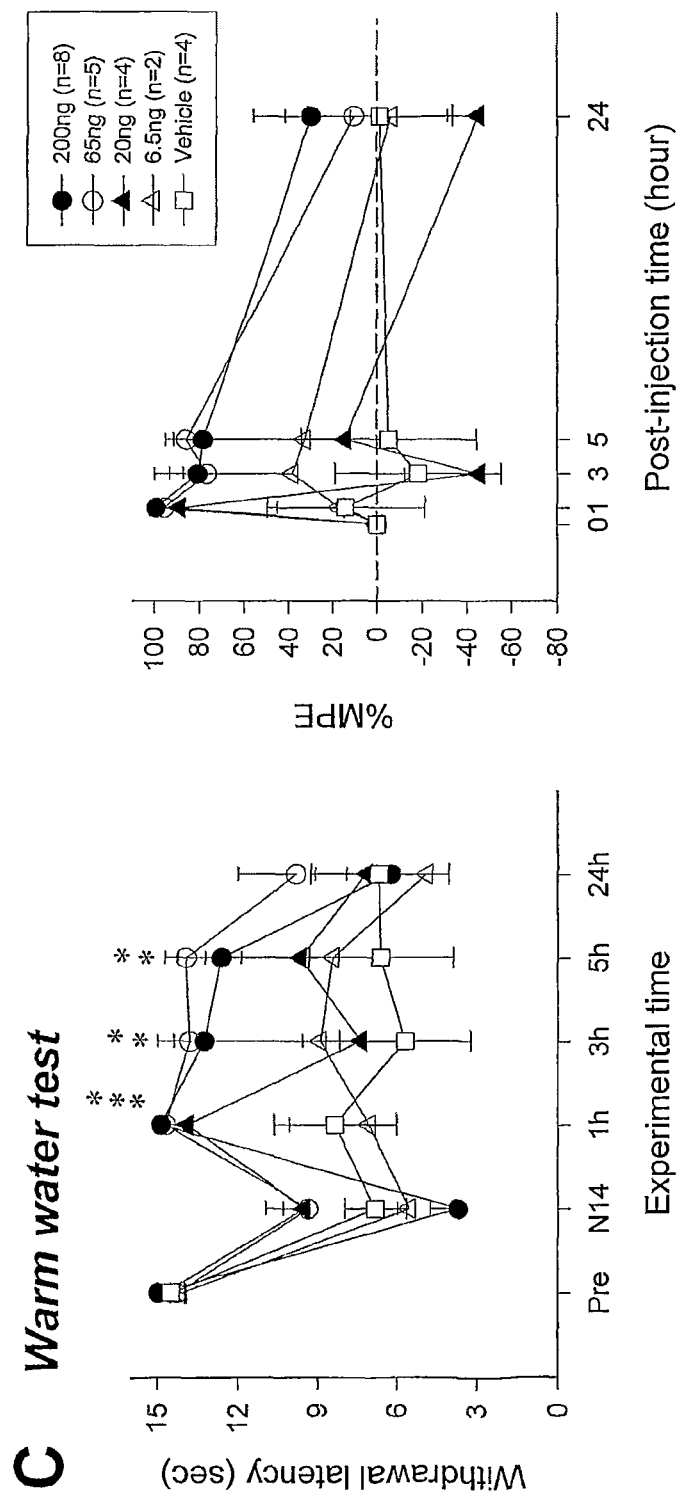

Mechanical allodynia was assessed by determining the stiffness (gram) of von Frey hairs to induce 50% avoidance (withdrawal) response after poking the tail with von Frey hairs. As represented in FIG. 11, the administration of either FVIA or MVIIA gives rise to the increase in 50% withdrawal threshold in the course of time, while the withdrawal threshold is decreased after 2 hr post-injection. It was also elucidated that the FVIA peptide induced to elevate 50% withdrawal threshold in a dose dependent manner (6.5, 20, 65 and 200 ng/kg), as shown in FIG. 12A. Furthermore, as represented in FIGS. 12B and 12C, the FVIA peptide exhibits analgesic effects on cold and warm allodynia.

These results demonstrate that the FVIA peptide have an excellent analgesic effects in two types of neuropathy model.

Adverse Effects on Cardiovascular System

Figure 13:
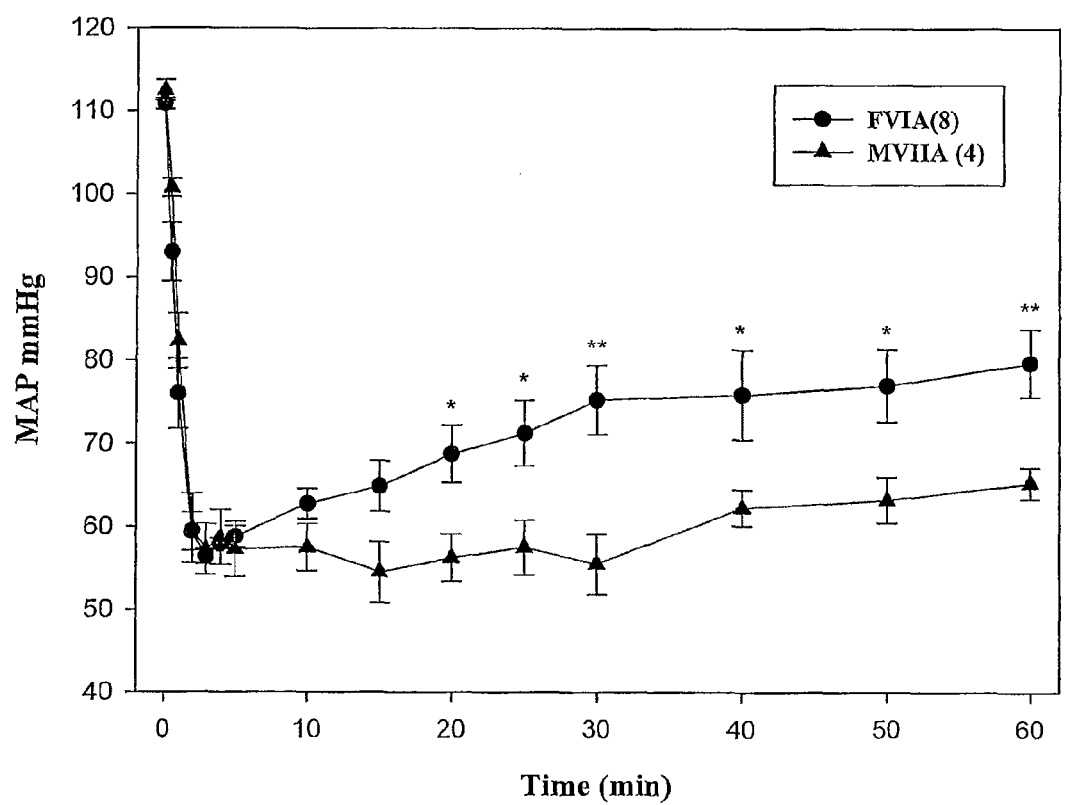
FIG. 13 represents mean arterial pressures (MAP) measured after the intravenous administration of 100 µg FVIA or MVIIA. Bar, standard error of mean.; *, P value compared with control (*P<0.05, P<0.01, *P<0.001).

Following the administration of either FVIA or MVIIA in a dose of 100 µg/kg, the mean arterial pressure (MAP) was monitored with time course. As shown in FIG. 13, the MVIIA peptide gives rise to a sharp decrease in MAP at an initial stage and slow recovery in MAP with the lapse of time. While the sharp decrease in MAP at an initial stage was also observed in the group administered with the FVIA, the FVIA peptide exhibited much better recovery in MAP.

Further Discussion

Conopeptides Isolation

Conopeptides consist of diverse families based on signal sequence and the Cys pattern. Two broad divisions of venom components are shown: disulfide-rich conotoxins and peptides that lack multiple disulfide cross-links [1].

Among these family, O and A superfamily discovered by the present inventors were more abundant than the other superfamily. The 26 of O-superfamily and 18 of A-superfamily were characterized by biochemical methods and gene cloning. The others were five of M-superfamily and a no disulfide peptide.

To characterize sequences of conopeptides, biochemical methods and gene cloning were used. Biochemical methods needed 20 more cone snails and laborious steps to purify single peptides. But novel posttranslational modification could be identified by Edman degradation and mass information. In addition, original disulfide pattern should be determined from native peptides. In gene cloning, only one cone snail was enough for cDNA library cloning but mature peptides would be deduced. Both methods were complementary to each other. The 50 peptides more were identified from Korean cone snail. Among them, the FVIA of the present invention is a sequence obtained by cloning a genomic DNA.

Assignments and Constraints of FVIA Structure

The sequential assignment was used to obtain the complete assignments. Gly residues were immediately identified by symmetrical arrangements in COSY spectrum. And $Thr^4$ and $Ala^{12}$ residues were also easily confirmed in TOCSY spectrum. The $NH_2$ of $Asn^{14}$ and δ- and ε-protons of $Tyr^{13}$ were identified and were useful in assignments. $NH_2$, present in TOCSY and COSY, was assigned to the amidated C-terminus of the peptide. But there were difficulties caused by peak overlapping and broadening. For example, $C_\alpha H$ of $Cys^1$, $Lys^2$ and $Lys^6$ (4.503 ppm) and NH of $Thr^{17}$ and $NH_2$ of C terminal (8.441 ppm) were overlapped. The peak broadenings of $Gly^{18}$ and $Gly^{23}$ hide surrounding peaks. These problems were overcome by comparing spectrums in different temperature, pH and mixing time of NOESY (Table 2).

The constraints used in the final calculations consisted of 128 intra-residue distances, 72 sequential distances, 84 non-sequential distances, 11 dihedral angle and 4 $\chi^1$ angle constraints obtained from coupling constant measurements. Stereospecific assignments of the β-methylene protons were obtained based on a combination of the $\chi^1$ angle coupling constant and NOE-derived distances between the $C_\beta H$ and NH.

Structure-Activity Relationships of FVIA and MVIIA

The N-type calcium channels play an important role in the control of neurotransmitter release from nerve terminals and are important drug targets for the treatment of pain and ischemic brain injury. And diverse isoforms have been reported [46-48]. The functions and organ distributions of these isoforms are different and peripheral form has importance related to reducing pains, especially.

The diverse conotoxins selectively block voltage-gated $Ca^{2+}$ channels and it provides valuable information about the functional diversity and structural determinants of the voltage sensitive channels. Among them, ω-conotoxins GVIA and MVIIA selectively bind to the external vestibules of the N-type calcium channel in the domain III S5-S6 region as pore blocker [8, 42, 44]. MVIIA (SNX111/Ziconotide/Prialt; Elan) is well known ω-conotoxins that is analgesic approved by FDA. But the side effects of MVIIA have been reported and Austria groups suggested that MVIIA is minutely specific to central isoform than peripheral on basis of washout experiments and it will be the reason of side-effects [14]. GVIA irreversibly binds to the calcium channel, so it was excluded in discussion.

Therefore, if MVIIA gained better reversibility, it would be better drug than present.

We started to study the structural and functional studies on these views. Our group has found 20 more O-superfamily conotoxins, having C—C—CC—C—C motif, by gene cloning and venom extractions. Among them, FVIA is most abundant results in gene cloning, so same sequence is found repetitively in cDNA library. And FVIA is highly similar with MVIIA. The six residues in the loop 1 and 2 of MVIIA and FVIA are different and the other is exactly same. These residues differences are expected to cause the structural difference in details and the functional difference including mechanism, potency and recovery following washout. And there would be molecular determinants related to potency and reversibility, respectively.

Figure 4:
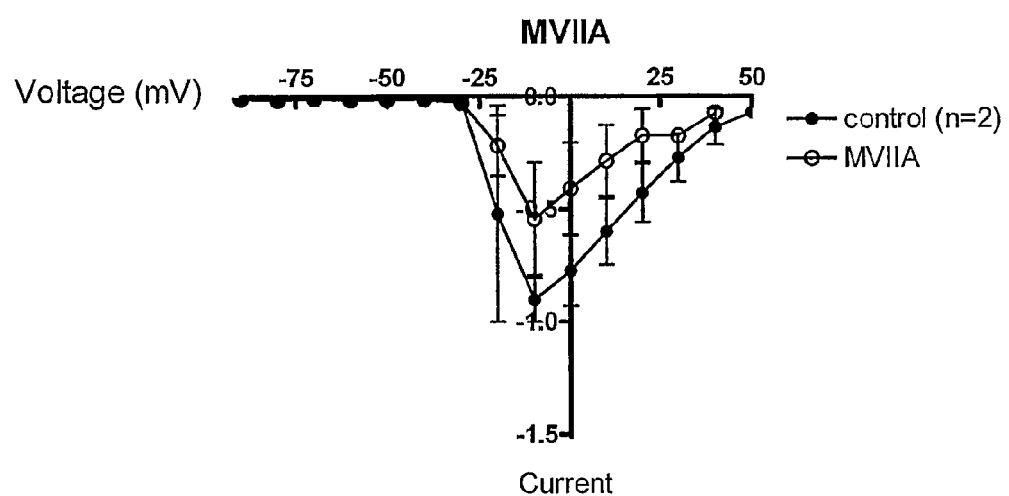
FIG. 4 is current-voltage curves of MVIIA (panel A) and FVIA (panel B). These figure show current inhibition without horizontal curve shift.
Figure 4:
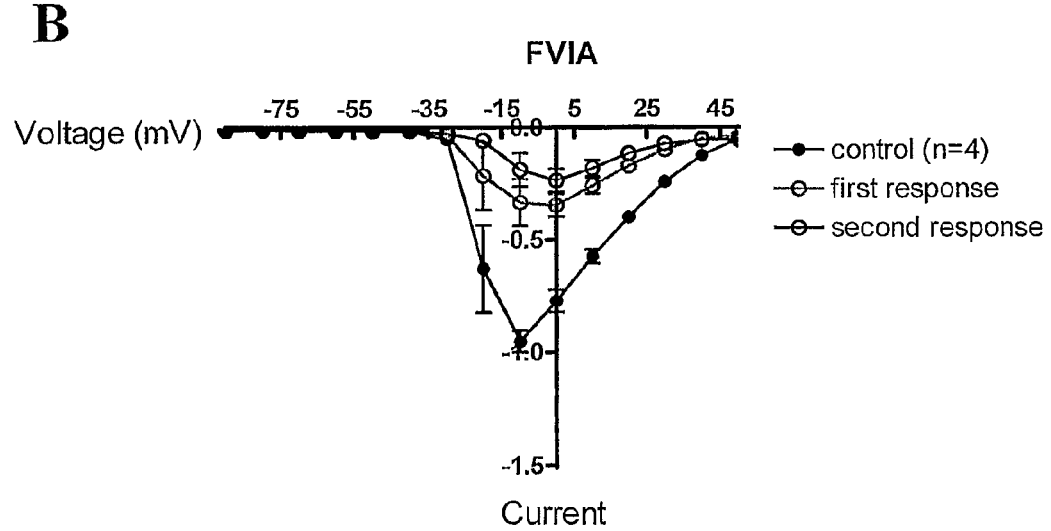

First, we check the potency on electrophysiology experiments. HEK 293 cells used expressed human N-type calcium channel directly related to human pain signaling and potency was represented by $IC_{50}$ values in dose-inhibition (response) curve. The $IC_{50}$ values of MVIIA and FVIA are very similar in nM scale. $Lys^2$, $Tyr^{13}$, $Arg^{10}$ and $Arg^{21}$ residues important in function are conserved in FVIA (FIG. 3), so these results were expected. Second, current-voltage curve experiments carried out. These results show that calcium channels in HEK 293 were expressed properly and the pore blocking mechanism of MVIIA and FVIA are same (FIG. 4). Lastly, washout following toxin injection was performed. Washout continued until reaching the stationary states. FIG. 5 shows that recovery from MVIIA (35%) is significantly different from FVIA (75%). It was interesting that the reversibility of these peptides is different despite similar potency. These facts show that the dissociation between the potency and reversibility could be possible and there would be distinct molecular determinants (in this case, residues) (FIG. 5).

For determining whether the structure difference affect above function or not, and which residues are important in these function and structure, $^1$H NMR experiments were carried out. We expected that fine structural difference occurs in loop 1 and especially loop 2, which is binding loop, caused by primary sequence difference. Although the whole topology is similar, the local structure of loop 2 is a little bit different, as we expected.

So, we consider the possibility that the structural difference of loop 2 affects the reversibility entirely, not by one residue difference. This structural difference was expected by different number of $^3J_{NH-C\alpha}$ coupling constants. For $^3J_{NH-C\alpha H}$ greater than 8.0 Hz, there are 11 and 9 in FVIA and MVIIA respectively [49]. Second, specific sequence $Asn^{14}$ ($Asp^{14}$) and $Ile^{11}$ ($Leu^{11}$) substitutions could cause the functional differences. $Asp^{14}$ is charged negatively, so the net change or local charge effect could affect the functional difference. $Leu^{11}$ in MVIIA is also important residues in activities [7]. Fine shift of methyl group of $Leu^{11}$ could weaken binding and make it easy to release from the channel in turns.

Analgesic Effects of FVIA

Pains can be classified into nociceptive, inflammatory and neuropathic pains according to etiological mechanisms. The nociceptive pains are caused by external stimuli and play a role in defending self from external harmful stimuli. The inflammatory pains are caused by pro-inflammatory molecules and the neuropathic pains caused by nerve injury. About 50 animal models have been already suggested for accessing such pains.

The FIVA peptide was examined to exert analgesic effect on nociceptive pains by tail flick test and plantar test developed for acute nociceptive pain caused by heat (FIGS. 8A and 8B).

Glutamate and substance P are one of neurotransmitters pivotal in signal transduction of pain. The intrathecal injection of these neurotransmitters induces pains. In tests using glutamate and substance P, the FVIA shows statistically significant analgesic effect (FIGS. 9A and 9B).

The intraperitoneal treatment of 1% acetic acid elicits nociceptive behavior such as writhing. The FVIA administration results in the decrease in writhing counts (FIG. 9C).

For formalin test, pains have two distinct phases: the first phase relating to nociceptive pains and the second phase relating to inflammatory pains. The mice administered with FVIA were observed to show significant analgesic effects on both the first phase and the second phase. Furthermore, the FVIA peptide is much more effective in the second phase relating to inflammatory pains than the first phase (FIG. 10A). The FVIA peptide shows analgesic effect in a dose-dependent manner, as represented in FIG. 10B. Interestingly, 100 ng of FVIA administered completely prevents pains in the second phase.

Rats with injured L5 and L6 spinal nerves or injured S1 and S2 spinal nerves are induced to have neuropathic pains and show hyperalgesia and allodynia symptoms. The FVIA increases 50% withdrawal threshold to mechanical allodynia induced by nerve injury depending on concentrations (FIGS. 11 and 12A). Also, the FVIA peptide shows analgesic effects on cold/warm allodynia, while its concentration dependent manner is weaker than mechanical allodynia (FIGS. 12B and 12C). It was elucidated that 6.5 ng FVIA exhibited anti-cold/warm allodynic effects similar to 200 ng FVIA, demonstrating that anti-cold/warm allodynic effect of FVIA may be shown through other mechanisms than its anti-mechanical allodynic effect, and is more sensitive.

In summary, the FVIA peptide could be appreciated to have relatively weaker analgesic effects on nociceptive pains, which was verified by tail flick test, plantar test and the first phase of formalin test. Unlikely, the FVIA peptide proves to be considerable drug candidates for inflammatory pains, which was examined by formalin test and tests using glutamate, substance P and acetic acid. In animal models with injured leg or tail nerves, the FVIA peptide is elucidated to exert significant analgesic effects on allodynia. Since nociceptive pains are one of defense mechanisms against outside harmful stimuli, it is not desirable to excessively inhibit nociceptive pains. It is generally known for one of skill in the art that excellent analgesic drug candidates exhibit pain relief potency selectively on inflammatory and neuropathic pains, one of pathologic pains.

Based on the experiment results described hereinabove, it could be concluded that the FVIA peptide or its analogues originated from Korean cone snails is a promising analgesic drug candidate.

Adverse Effects of FVIA

MVIIA is one of commercially accessible ω-conotoxins that is analgesic approved by FDA in the year of 2004 (Prialt, Elan Corp.). However, the severe side effects and administration mode of MVIIA makes its administration restrictive. For example, MVIIA has been reported to have adverse effects associated with (i) nerve system caused by inhibiting N-type VSCCs of central nerve system and (ii) cardiovascular system caused by inhibiting autonomic nerve system to affect blood pressure and pulse rate.

We monitored the mean arterial pressure (MAP) following the administration of either FVIA or MVIIA for accessing adverse effects on cardiovascular system. Both peptides were analyzed to give rise to a sharp decrease in MAP at an initial stage. However, with the lapse of time, the MAP of the group administered with FVIA was shown to reach the initial normal arterial pressure very slowly. On the contrary, the MVIIA peptide showed worse recovery and resulted in the relatively low arterial pressure around 60 mmHg. This adverse effect of MVIIA would be ascribed to its low reversibility.

Accordingly, these results urge us to conclude that the FVIA peptide or its analogues are an excellent analgesic drug candidate in the sense that they have a calcium channel blocking potency similar to MVIIA and a much less side effects than MVIIA.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Heinrich Terlau and Baldomero M. Olivera (2004) Physiol Rev 84, 41-68
2. William R. Gray and Baldomero M. Olivera (1988) Ann. Rev. Biochem. 57, 665-700
3. Richard J. Lewis and Maria L. Garcia (2003) Nature Drug Disc. 2, 1-13
4. Baldomero M. Olivera (1997) Molecular Biology of the Cell 8, 2101-2109
5. Baldomero M. Olivera (2002) Annu. Rev, Ecol. Syst. 33, 25-47
6. D. Alonso and B. G. Livett (2003) Mini Reviews in Medicinal Chem. 3, 785-787
7. Katherine J. Nielsen and Richard Lewis (2000) J. Mol. Recognit. 13, 55-70
8. Zhong-Ping Feng and Gerald W. Zampoin (2003) J. Biol. Chem. 278, 20171-20178
9. Penn, R. D. and Paice, J. A. (2000) Pain. 85, 291-296
10. Jain, K. K. (2000) Expert. Opin. Investig. Drugs 9, 2403-2401
11. Levin, T. and Bailine, S. (2002) Psychosomatics. 43, 63-66
12. Richard J. Lewis, Katherine J. Nielsen, David J. Craik, Marion L. Loughnan, Denise A. Adams, Iain A. Sharpe, Tudor Luchian, David J. Adams, Trudy Bond, Linda Thomas, Alun Jones, Jodi-Lea Matheson, Roger Drinkwater, Peter R. Andrews, and Paul F. Alewood (2000) J. Biol. Chem. 275, 35335-35344
13. David J. Adams, Amanda B. Smith, Christina I. Schroeder, Takahiro Yasuda, and Richard J. Lewis (2003) J. Biol. Chem. 278, 4057-4062
14. Jorgen Mould, Takahiro Yasuda, Christina I. Schroeder, Aaron M. Beedle, Clinton J. Doering, Gerald W. Zamponi, David J. Adams, and Richard J. Lewis (2004) J. Biol. Chem. 279, 34705-34714
15. Laszlo Nadasdi and J. Ramachandran (1995) Biochemistry. 34, 8076-8081
16. H. Jijakli and W. J. Malaisse (1996) Pharmacological Research. 34, 105-108
17. Jae Il Kim and Kazuki Sato (1995) Biochem. Biophys. Res. Commun. 206, 449-454
18. Jae Il Kim and Kazuki Sato (1997) Biochem. Biophys. Res. Commun. 230, 133-135
19. Larry A. Compton and W. Curtis Johnson, J R. (1985) Anal. Biochem. 155, 155-167
20. Taehyun Kim and Hyewhon Rhim (2004) Biochem. Biophys. Res. Commun. 324, 401-408
21. Marion, D. and Wüthrich, K. (1983) Biochem. Biophys. Res. Commun. 113, 967-974
22. Bax, A. and Davis, D. G. (1985) J. Magn. Reson. 65, 355-359
23. Jeener, J., Meier, B. H., Bachmann, P. and Ernst, R. R. (1979) J. Chem. Phys. 71, 4546-4553
24. Macura, S., Huang, Y., Suter, D. And Ernst, R. R. (1981) J. Magn. Reson. 43, 259-281
25. Piotto, M., Saudek, V. and Sklenar, V. (1992) J. Biomol. NMR. 2, 661-665
26. Rance, M., Sorensen, O. W., Bodenhausen, G., Wagner, G., Ernst, R. R. and Wüthrich, K. (1983) Biochem. Biophys. Res. Commun. 117, 479-485
27. Mueller, L. (1987) J. Magn. Reson. 72, 191-196
28. Wüthrich, K., Billeter, M. and Braun, W. (1983) J. Mol. Biol. 169, 949-961
29. Clore, M., Gronenborn, A. M., Nilges, M. and Ryan, C. A. (1987) Biochemistry. 26, 8012-8023
30. Nilges, M., Gronenborn, A. M, Brünger, A. T. and Clore, M. (1998) Protein Eng. 2, 27-38
31. Pardi, A., Billerter, M. and Wüthrich, K. (1984) J. Mol. Biol. 180, 741-751
32. Kline, A. D., Braun, W. and Wüthrich, K. (1988) J. Mol. Biol. 204, 675-724
33. Hyberts, S. G., Marki, W. and Wagner, G. (1987) Eur. J. Biochem. 164, 625-635
34. Wagner, G., Braun, W., Havel, T. F., Schaumann, T., Go, N. and Wüthrich, K. (1987) J. Mol. Biol. 196, 611-639
35. Fletcher, J. I., Smith, R., O'Donoghue, S. I., Nilges, M., Conner, M. and Ilowden, M. E. H. et al. (1997) Nature Struct. Biol. 4, 559-566
36. Fletcher, J. I., Chapman, B. E., Mackay, J. P., Howden, M. E. H. and King, G. F. (1997) Structure 5, 1525-1535
37. Brunger, A. T., (1992) X-PLOR Manual, Version 3.1, Yale University, New Haven, Conn.
38. Laskowski, R. A., Rullmann, J. A., MacArthur, M. W., Kaptein, R. and Thornton, J. M. (1996) J. Biomol. NMR. 8, 477-486
39. Hutchinson, E. G. and Thornton, J. M. (1996) Protein Sci. 5, 212-220
40. Koradi, R., Billeter, M. and Wuthrich, K. (1996) J. Mol. Graph. 14, 29-32
41. Hyberts, S. G., Goldberg, M. S., Havel, T. F. and Wagner, G. (1992) Protein Sci. 1, 736-751
42. Patrick T. Ellinor, Ji-Fang Zhang, William A. Horne and Richard W. Tsien (1994) Nature. 372, 272-275
43. Wüthrich, K. (1986) NMR of Proteins and Nucleic Acids, John Wiley & Sons, Inc., New York
44. Feng, Z. P., Hamid, J., Doering, C., Jarvis, S. E., Bosey, G. M., Bourinet, E., Snutch, T. P., and Zamponi, Z. W. (2001) J. Biol. Chem. 276, 5726-5730
45. Jane S. Richardson (1981) Advances in Protein Chemistry. Vol. 34 167-339
46. Lin, Z., Haus, S., Edgerton, J., and Lipscombe, D. (1997) Neuron 18, 153166
47. Lin, Z., Lin, Y., Schorge, S., Pan, J. Q., Beierlein, M., and Lipscombe, D. (1999) J. Neurosci. 19, 53225331
48. Kaneko, S., Cooper, C. B., Nishioka, N., Yamasaki, H., Suzuki, A., Jarvis, S. E., Akaike, A., Satoh, M., and Zamponi, G. W. (2002) J. Neurosci. 22, 8292
49. Vladimir J. Basus, Laszlo Nadasdi, J. Ramachandran, George P. Miljanich (1995) FEBS Letters 370, 163169
50. Hylden J L and Wilcox G L. (1980) *Eur. J. Pharmacol*, 67:313-6
51. Hylden J L and Wilcox G L. (1981) *Brain Res.* 217:212-5
52. Hunskaar (1985) *J. Neurosci. Methods,* 14:69-76
53. Kim S H and Chung J M (1992) *Pain,* 50:355-363
54. Yaksh T L and Rudy T A. (1976) *Physiol. Behav.,* 17:1031-6
55. Dixon, W. J. (1980) *Annu. Rev. Pharmocol Toxicol.* 20, pp. 441-462.
56. Na H S (1994) *Neurosci Lett,* 177:50-52.
57. Chaplan (1994) *J Neurosci Methods* 53:55-63.

What is claimed is:

1. A method for preventing or treating chronic pain conditions, acute pain, post-operative pain or high blood pressure in a subject, which comprises administering to the subject in need of such treatment a pharmaceutical composition comprising (a) a therapeutically effective amount of an ω-conotoxin peptide that has increased binding reversibility to an N-type calcium channel and comprises an amino acid sequence represented by the following general formula III:

Formula III

Cys-Lys-Xaa$_1$-Xaa$_2$-Gly-Xaa$_3$-Xaa$_4$-Cys-Xaa$_5$-Xaa$_6$-Ile-Ala-Tyr-Xaa$_9$-Cys-Cys-Xaa$_{10}$-Xaa$_{11}$-Xaa$_{12}$-Cys-Xaa$_{13}$-Xaa$_{14}$-Xaa$_{15}$-Xaa$_{16}$-Cys  (SEQ ID NO:16)

wherein Xaa$_1$ is Gly; Xaa$_2$ is Thr or Lys; Xaa$_3$ is Lys or Ala; Xaa$_4$ is Ser or Lys; Xaa$_5$ is Ser or Arg; Xaa$_6$ is Arg; Xaa$_9$ is Asn; Xaa$_{10}$ is Thr, Xaa$_{11}$ is Gly; Xaa$_{12}$ is Ser; Xaa$_{13}$ is Arg; Xaa$_{14}$ is Ser; Xaa$_{15}$ is Gly; and Xaa$_{16}$ is Lys or Arg, and (b) a pharmaceutically acceptable carrier, wherein administration of said ω-conotoxin peptide treats said chronic pain conditions, acute pain, post-operative pain, or high blood pressure.

2. The method of claim 1, wherein said w-conotoxin peptide consists of the amino acid sequence of SEQ ID NO:17.

* * * * *

SEQUENCE LISTING

<160> NUMBER OF SEQ ID NOS: 17

<210> SEQ ID NO 1
<211> LENGTH: 25
<212> TYPE: PRT
<213> ORGANISM: Conus Flavidus

<400> SEQUENCE: 1

```
Cys Lys Gly Thr Gly Lys Ser Cys Ser Arg Ile Ala Tyr Asn Cys Cys
1               5                   10                  15

Thr Gly Ser Cys Arg Ser Gly Lys Cys
            20                  25
```

<210> SEQ ID NO 2
<211> LENGTH: 25
<212> TYPE: PRT
<213> ORGANISM: Artificial Sequence
<220> FEATURE:
<223> OTHER INFORMATION: Chimera-MFMM

<400> SEQUENCE: 2

```
Cys Lys Gly Lys Gly Ala Lys Cys Ser Arg Ile Ala Tyr Asn Cys Cys
1               5                   10                  15

Thr Gly Ser Cys Arg Ser Gly Lys Cys
            20                  25
```

<210> SEQ ID NO 3
<211> LENGTH: 25
<212> TYPE: PRT
<213> ORGANISM: Artificial Sequence
<220> FEATURE:
<223> OTHER INFORMATION: FVIA[N14D]

<400> SEQUENCE: 3

```
Cys Lys Gly Thr Gly Lys Ser Cys Ser Arg Ile Ala Tyr Asp Cys Cys
1               5                   10                  15

Thr Gly Ser Cys Arg Ser Gly Lys Cys
            20                  25
```

<210> SEQ ID NO 4
<211> LENGTH: 75
<212> TYPE: DNA
<213> ORGANISM: Conus Flavidus

<400> SEQUENCE: 4

```
tgcaagggta caggaaaatc atgcagtagg attgcatata actgctgcac cggttcttgc     60
agatcgggta aatgt                                                      75
```

<210> SEQ ID NO 5
<211> LENGTH: 25
<212> TYPE: PRT
<213> ORGANISM: Artificial Sequence
<220> FEATURE:
<223> OTHER INFORMATION: MVIIA

<400> SEQUENCE: 5

```
Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25
```

<210> SEQ ID NO 6

```
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(4)
<223> OTHER INFORMATION: Xaa can be any amino acid
<220> FEATURE:
<221> NAME/KEY: MISC_FEATURE
<222> LOCATION: (6)..(7)
<223> OTHER INFORMATION: Xaa can be any amino acid
<220> FEATURE:
<221> NAME/KEY: MISC_FEATURE
<222> LOCATION: (9)..(12)
<223> OTHER INFORMATION: Xaa can be any amino acid
<220> FEATURE:
<221> NAME/KEY: MISC_FEATURE
<222> LOCATION: (14)..(14)
<223> OTHER INFORMATION: Xaa can be any amino acid
<220> FEATURE:
<221> NAME/KEY: MISC_FEATURE
<222> LOCATION: (17)..(19)
<223> OTHER INFORMATION: Xaa can be any amino acid
<220> FEATURE:
<221> NAME/KEY: MISC_FEATURE
<222> LOCATION: (21)..(24)
<223> OTHER INFORMATION: Xaa can be any amino acid

<400> SEQUENCE: 6

Cys Lys Xaa Xaa Gly Xaa Xaa Cys Xaa Xaa Xaa Xaa Tyr Xaa Cys Cys
1               5                   10                  15

Xaa Xaa Xaa Cys Xaa Xaa Xaa Xaa Cys
            20                  25

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid

<400> SEQUENCE: 7

Xaa Xaa Ile Ala Tyr Xaa
1               5

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Gly or Ser
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (6)..(7)
<223> OTHER INFORMATION: Xaa can be any amino acid
<220> FEATURE:
<221> NAME/KEY: MISC_FEATURE
```

-continued

```
<222> LOCATION: (9)..(10)
<223> OTHER INFORMATION: Xaa can be any amino acid
<220> FEATURE:
<221> NAME/KEY: MISC_FEATURE
<222> LOCATION: (14)..(14)
<223> OTHER INFORMATION: Xaa can be any amino acid
<220> FEATURE:
<221> NAME/KEY: MISC_FEATURE
<222> LOCATION: (17)..(19)
<223> OTHER INFORMATION: Xaa can be any amino acid
<220> FEATURE:
<221> NAME/KEY: MISC_FEATURE
<222> LOCATION: (21)..(24)
<223> OTHER INFORMATION: Xaa can be any amino acid

<400> SEQUENCE: 8

Cys Lys Xaa Xaa Gly Xaa Xaa Cys Xaa Xaa Ile Ala Tyr Xaa Cys Cys
1               5                   10                  15

Xaa Xaa Xaa Cys Xaa Xaa Xaa Xaa Cys
            20                  25

<210> SEQ ID NO 9
<211> LENGTH: 25
<212> TYPE: PRT
<213> ORGANISM: Artificial Sequence
<220> FEATURE:
<223> OTHER INFORMATION: CVIA

<400> SEQUENCE: 9

Cys Lys Ser Thr Gly Ala Ser Cys Arg Arg Thr Ser Tyr Asn Cys Cys
1               5                   10                  15

Thr Gly Ser Cys Arg Ser Gly Arg Cys
            20                  25

<210> SEQ ID NO 10
<211> LENGTH: 27
<212> TYPE: PRT
<213> ORGANISM: Artificial Sequence
<220> FEATURE:
<223> OTHER INFORMATION: GVIA

<400> SEQUENCE: 10

Cys Lys Ser Pro Gly Ser Ser Cys Ser Pro Thr Ser Tyr Asn Cys Cys
1               5                   10                  15

Arg Ser Cys Asn Pro Tyr Thr Lys Arg Cys Tyr
            20                  25

<210> SEQ ID NO 11
<211> LENGTH: 27
<212> TYPE: PRT
<213> ORGANISM: Artificial Sequence
<220> FEATURE:
<223> OTHER INFORMATION: CVID

<400> SEQUENCE: 11

Cys Lys Ser Lys Gly Ala Lys Cys Ser Lys Leu Met Tyr Asp Cys Cys
1               5                   10                  15

Ser Gly Ser Cys Ser Gly Thr Val Gly Arg Cys
            20                  25

<210> SEQ ID NO 12
<211> LENGTH: 25
<212> TYPE: PRT
<213> ORGANISM: Artificial Sequence
<220> FEATURE:
<223> OTHER INFORMATION: Chimera-FMFF

<400> SEQUENCE: 12
```

Cys Lys Gly Thr Gly Lys Ser Cys Ser Arg Leu Met Tyr Asp Cys Cys
1               5                   10                  15

Thr Gly Ser Cys Arg Ser Gly Lys Cys
            20                  25

<210> SEQ ID NO 13
<211> LENGTH: 25
<212> TYPE: PRT
<213> ORGANISM: Artificial Sequence
<220> FEATURE:
<223> OTHER INFORMATION: FVIA[I11L, A12M]

<400> SEQUENCE: 13

Cys Lys Gly Thr Gly Lys Ser Cys Ser Arg Leu Met Tyr Asn Cys Cys
1               5                   10                  15

Thr Gly Ser Cys Arg Ser Gly Lys Cys
            20                  25

<210> SEQ ID NO 14
<211> LENGTH: 21
<212> TYPE: DNA
<213> ORGANISM: Artificial Sequence
<220> FEATURE:
<223> OTHER INFORMATION: Synthetic Construct

<400> SEQUENCE: 14
ctctctctct ctctgctgga c                                         21

<210> SEQ ID NO 15
<211> LENGTH: 24
<212> TYPE: DNA
<213> ORGANISM: Artificial Sequence
<220> FEATURE:
<223> OTHER INFORMATION: Synthetic Construct

<400> SEQUENCE: 15
cagaaaagga tagagcacag aagg                                      24

<210> SEQ ID NO 16
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Thr or Lys
<220> FEATURE:
<221> NAME/KEY: MISC_FEATURE
<222> LOCATION: (6)..(6)
<223> OTHER INFORMATION: Xaa is Lys or Ala
<220> FEATURE:
<221> NAME/KEY: MISC_FEATURE
<222> LOCATION: (7)..(7)
<223> OTHER INFORMATION: Xaa is Ser or Lys
<220> FEATURE:
<221> NAME/KEY: MISC_FEATURE
<222> LOCATION: (9)..(9)
<223> OTHER INFORMATION: Xaa is Ser or Arg
<220> FEATURE:
<221> NAME/KEY: MISC_FEATURE
<222> LOCATION: (10)..(10)
<223> OTHER INFORMATION: Xaa is Arg
<220> FEATURE:
<221> NAME/KEY: MISC_FEATURE

```
<222> LOCATION: (14)..(14)
<223> OTHER INFORMATION: Xaa is Asn or Asp
<220> FEATURE:
<221> NAME/KEY: MISC_FEATURE
<222> LOCATION: (17)..(17)
<223> OTHER INFORMATION: Xaa is Thr
<220> FEATURE:
<221> NAME/KEY: MISC_FEATURE
<222> LOCATION: (18)..(18)
<223> OTHER INFORMATION: Xaa is Gly
<220> FEATURE:
<221> NAME/KEY: MISC_FEATURE
<222> LOCATION: (19)..(19)
<223> OTHER INFORMATION: Xaa is Ser
<220> FEATURE:
<221> NAME/KEY: MISC_FEATURE
<222> LOCATION: (21)..(21)
<223> OTHER INFORMATION: Xaa is Arg
<220> FEATURE:
<221> NAME/KEY: MISC_FEATURE
<222> LOCATION: (22)..(22)
<223> OTHER INFORMATION: Xaa is Ser
<220> FEATURE:
<221> NAME/KEY: MISC_FEATURE
<222> LOCATION: (23)..(23)
<223> OTHER INFORMATION: Xaa is Gly
<220> FEATURE:
<221> NAME/KEY: MISC_FEATURE
<222> LOCATION: (24)..(24)
<223> OTHER INFORMATION: Xaa is Lys or Arg

<400> SEQUENCE: 16

Cys Lys Xaa Xaa Gly Xaa Xaa Cys Xaa Xaa Ile Ala Tyr Xaa Cys Cys
1               5                   10                  15

Xaa Xaa Xaa Cys Xaa Xaa Xaa Xaa Cys
            20                  25

<210> SEQ ID NO 17
<211> LENGTH: 25
<212> TYPE: PRT
<213> ORGANISM: Artificial Sequence
<220> FEATURE:
<223> OTHER INFORMATION: Chimera-MFMM

<400> SEQUENCE: 17

Cys Lys Gly Lys Gly Ala Lys Cys Ser Arg Ile Ala Tyr Asn Cys Cys
1               5                   10                  15

Thr Gly Ser Cys Arg Ser Gly Lys Cys
            20                  25
```